(12) United States Patent
Raj et al.

(10) Patent No.: US 12,714,841 B2
(45) Date of Patent: Aug. 25, 2026

(54) DISINFECTING CAP FOR NEEDLELESS CONNECTORS WITH MULTI-PART HOUSING AND AUTOMATIC LOCK

(71) Applicant: Becton, Dickinson and Company, Franklin Lakes, NJ (US)

(72) Inventors: Ashita Raj, Bangalore (IN); Karthik MR, Bangalore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 800 days.

(21) Appl. No.: 18/084,639

(22) Filed: Dec. 20, 2022

(65) Prior Publication Data

US 2024/0198075 A1 Jun. 20, 2024

(51) Int. Cl.
*A61M 39/16* (2006.01)
*A61M 39/20* (2006.01)

(52) U.S. Cl.
CPC .......... *A61M 39/162* (2013.01); *A61M 39/20* (2013.01); *A61M 2207/10* (2013.01)

(58) Field of Classification Search
CPC ..... A61M 39/162; A61M 39/20; A61M 39/16
See application file for complete search history.

(56) References Cited

U.S. PATENT DOCUMENTS 6,520,935 B1 2/2003 Jansen et al.
8,671,496 B2 3/2014 Vaillancourt et al.
8,696,820 B2 4/2014 Vaillancourt et al.
8,740,864 B2 6/2014 Hoang et al.
9,039,989 B2 5/2015 Liu et al.
9,283,369 B2 3/2016 Ma et al.
9,352,140 B2 5/2016 Kerr et al.
9,399,125 B2 7/2016 Burkholz
9,480,833 B2 11/2016 Hoang et al.
D834,187 S 11/2018 Ryan
10,376,686 B2 8/2019 Burkholz et al.
10,413,716 B2 9/2019 Sathe
10,871,246 B2 12/2020 Marici et al.
11,083,847 B2 8/2021 Mahmoodian
11,083,883 B2 8/2021 Ryan et al.
11,273,298 B2 3/2022 Erekovcanski et al.
11,344,715 B2 5/2022 Erekovcanski et al.
11,353,147 B2 6/2022 Marici et al.
(Continued)

FOREIGN PATENT DOCUMENTS

JP 2019503233 A 2/2019

*Primary Examiner* — Bradley J Osinski
(74) *Attorney, Agent, or Firm* — Servilla Whitney LLC

(57) ABSTRACT

A disinfecting cap for a needleless connector includes an outer housing having a sidewall and an outer guide on an inner surface of the sidewall. The cap also includes an inner housing having an open end sized to receive a distal end of the needleless connector, a sidewall, and an inner guide on an outer surface of the sidewall that interacts with the outer guide of the outer housing. The cap also includes an absorbent member disposed in the inner housing configured to contain a cleaning solution for cleaning and/or disinfecting portions of the needleless connector engaged to the cap. Movement of the inner guide relative to the outer guide causes the inner housing to move axially into the outer housing and to alternate between rotating in a first direction and rotating in a second direction relative to the outer housing.

20 Claims, 14 Drawing Sheets

(56) References Cited

U.S. PATENT DOCUMENTS

| | | | |
|---|---|---|---|
| 11,389,636 | B2 * | 7/2022 | Coyle .................. A61M 39/20 |
| D965,777 | S | 10/2022 | Marici et al. |
| 2012/0302968 | A1 | 11/2012 | Tennican |
| 2012/0302997 | A1 | 11/2012 | Gardner et al. |
| 2013/0035667 | A1 | 2/2013 | Anderson et al. |
| 2013/0178804 | A1 | 7/2013 | Tennican |
| 2013/0197485 | A1 | 8/2013 | Gardner et al. |
| 2014/0135739 | A1 | 5/2014 | Solomon et al. |
| 2015/0005699 | A1 | 1/2015 | Burbank et al. |
| 2015/0086441 | A1 | 3/2015 | She et al. |
| 2016/0106968 | A1 | 4/2016 | Solomon et al. |
| 2016/0144118 | A1 | 5/2016 | Solomon et al. |
| 2016/0310720 | A1 | 10/2016 | Solomon et al. |
| 2018/0055962 | A1 | 3/2018 | Drmanovic |
| 2018/0064604 | A1 | 3/2018 | Drmanovic |
| 2018/0071508 | A1 | 3/2018 | Drmanovic |
| 2018/0085568 | A1 | 3/2018 | Drmanovic |
| 2018/0200500 | A1 | 7/2018 | Ziebol et al. |
| 2018/0214242 | A1 | 8/2018 | Davis et al. |
| 2018/0214684 | A1 | 8/2018 | Avula et al. |
| 2018/0250194 | A1 | 9/2018 | Drmanovic |
| 2018/0256804 | A1 | 9/2018 | Burbank et al. |
| 2018/0256880 | A1 | 9/2018 | Follman et al. |
| 2018/0256881 | A1 | 9/2018 | Hitchcock et al. |
| 2018/0256883 | A1 | 9/2018 | Follman et al. |
| 2018/0369562 | A1 | 12/2018 | Gardner et al. |
| 2019/0038888 | A1 | 2/2019 | Gardner |
| 2019/0099593 | A1 | 4/2019 | Avula et al. |
| 2019/0117332 | A1 | 4/2019 | Davis et al. |
| 2019/0201681 | A1 | 7/2019 | Ziebol et al. |
| 2019/0262525 | A1 | 8/2019 | Wyeth et al. |
| 2019/0282795 | A1 | 9/2019 | Fangrow |
| 2019/0351212 | A1 | 11/2019 | Dudar et al. |
| 2020/0121858 | A1 | 4/2020 | Anderson et al. |
| 2020/0139037 | A1 | 5/2020 | Ziebol et al. |
| 2020/0155794 | A1 | 5/2020 | Ziebol |
| 2020/0197686 | A1 | 6/2020 | Anderson et al. |
| 2020/0238070 | A1 | 7/2020 | Ryan |
| 2020/0276346 | A1 | 9/2020 | Drmanovic |
| 2021/0001110 | A1 | 1/2021 | Bedoe et al. |
| 2021/0008237 | A1 | 1/2021 | Okman et al. |
| 2021/0008283 | A1 | 1/2021 | San Solo et al. |
| 2021/0093791 | A1 | 4/2021 | Anderson et al. |
| 2021/0138222 | A1 | 5/2021 | Jiang et al. |
| 2021/0138224 | A1 | 5/2021 | Marici |
| 2021/0187266 | A1 | 6/2021 | Ryan |
| 2021/0275707 | A1 | 9/2021 | Jiang et al. |
| 2021/0322749 | A1 | 10/2021 | Rothenberg et al. |
| 2021/0322750 | A1 | 10/2021 | Harandi et al. |
| 2021/0322751 | A1 | 10/2021 | Jiang et al. |
| 2021/0322752 | A1 | 10/2021 | Jiang et al. |
| 2022/0233836 | A1 | 7/2022 | Leibowitz |
| 2022/0273881 | A1 | 9/2022 | Mahmoodian et al. |

* cited by examiner 10
18
28
28
12
24
22
26
20
46
32

14
38
34
30
48
16
52

10
12
14
18
20
28
30
32
40
42

10
12
14
18
20
28
30
32
40
42
A2
A3

10
12
14
18
20
28
30
32
40
42
A5
A1

14
36
62
34
38
64

62
36
64

14
38
34
36
30
32

10
12
14
114
110
122

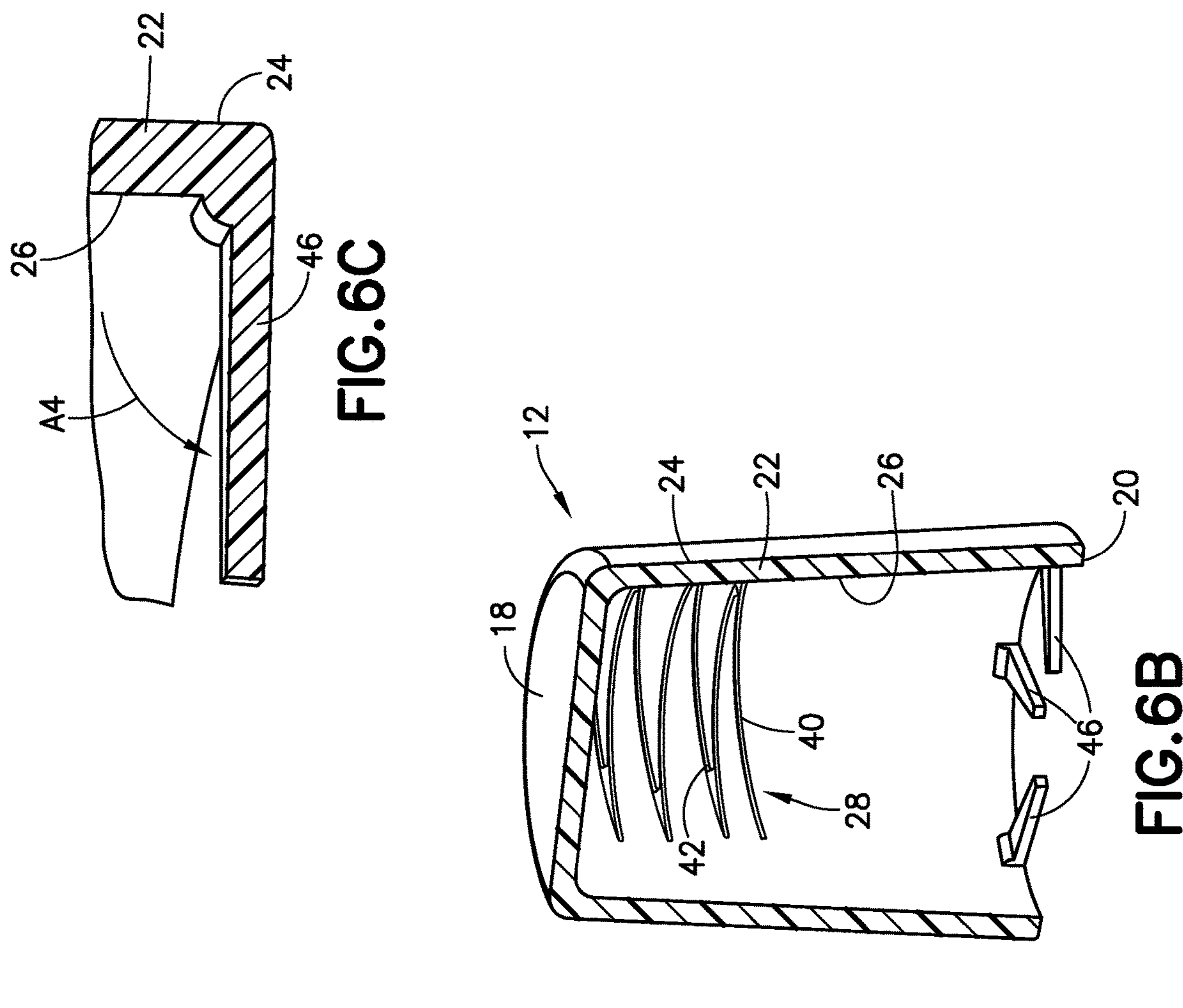
FIG.6C
FIG.6B
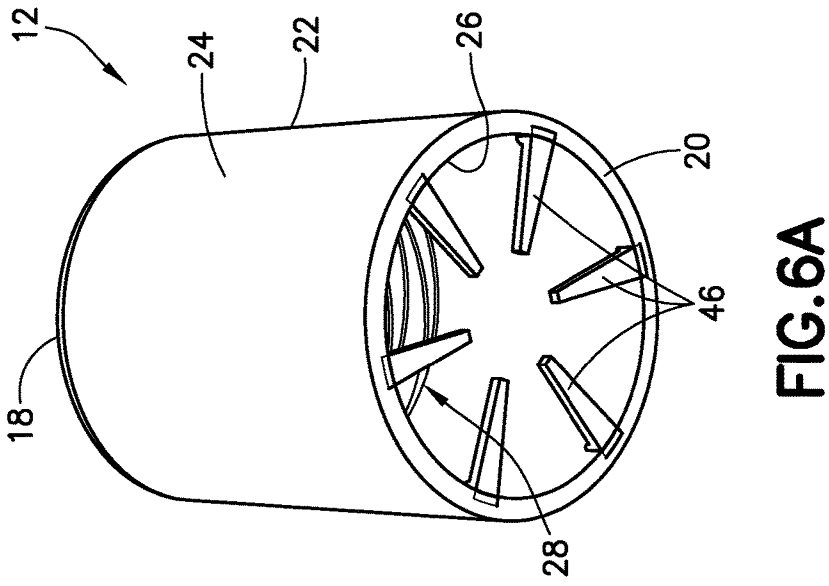
FIG.6A 56
60
58

10
12
14
56
60
32
58
18

30
24
22
26
20

212
222
218
220
210
218
220
222

DISINFECTING CAP FOR NEEDLELESS CONNECTORS WITH MULTI-PART HOUSING AND AUTOMATIC LOCK

BACKGROUND OF THE INVENTION

Field of the Invention

The present disclosure relates generally to caps for medical connectors and, in particular, to a cap configured to be attached to a needleless connector for sealing, cleaning or scrubbing, and disinfecting portions of the connector.

Description of Related Art

Vascular access devices (VADs) are commonly used medical devices, which can include intravenous (IV) catheters, such as peripheral catheters or central venous catheters. If not properly maintained or if exposed to a non-sterile environment, the VADs can become contaminated, sealed with blood clots, and/or can spread infection. Further, bacteria and other microorganisms may enter into a patient's vascular system from access hubs, ports, or valves upon connection to the VAD to deliver a fluid or pharmaceutical to a patient. Therefore, each access hub, port, valve, or other connection configured for attachment to a VAD is associated with some risk of transmitting a catheter related bloodstream infection (CRBSI) to a patient.

Many medical facilities implement sterile practices and protocols to ensure that VADs and access hubs or ports are used properly and do not become sealed or infected. These protocols often include sterilizing the access hubs, ports, and VADs, as well as flushing the catheter with a flush solution prior to use. Specifically, VAD standards of practice usually recommend flush procedures be performed after catheter placement, before fluid infusion, and before and after drug administration, blood sampling, transfusions, and/or administration of parenteral nutrition. Standards of practice can also require that access hubs, ports, and valves be capped with disinfection caps when not in use, to prevent microbial ingress into the hub, port, or valve and to sterilize areas of the hub, port, or valve that contact the VAD. Disinfecting caps are disposable cap devices that contain an amount of cleaning or disinfecting solution for sterilizing portions of the port, hub, and valve. Disinfecting caps can also include abrasive surfaces, inserts, members, or structures for mechanically removing particles, such as dust, dirt, microorganisms, cells, and other debris from surfaces of the hubs or ports of the VAD. In particular, mechanically removing or scrubbing biological materials, such as microorganisms and cells, from surfaces of the hubs and ports more fully exposes these materials to the cleaning or disinfecting solution to destroy such biological materials.

Access hubs and ports can have a variety of different types of connectors for securing the hub or port to the VAD. Currently, practitioners often carry several types of caps with them so that they can cap different types of hubs and ports, which may all be used for a particular patient. For example, caps for male needleless connectors and female needleless connectors, as well as IV and hemodialysis lines, often use different connector designs and may require different caps. There can be "male disinfecting cap devices" for disinfecting IS0594-2 type of female threaded fluid luer connectors and "female disinfecting cap devices" for disinfecting IS0594-2 type of male threaded fluid luer connectors.

Some examples of universal caps that fit on both male and female connectors are known. For example, U.S. Pat. No. 10,871,246, entitled "Universal connector or cap for male and female threaded fittings," which is incorporated herein by reference in its entirety, discloses a cap including a threaded protrusion that can engage both a male connector and a female connector. However, there is a need for simpler cap designs that can be manufactured inexpensively and efficiently, and which can be used with connectors having a variety of thread patterns, dimensions, and arrangements. The disinfecting caps of the present disclosure are configured to attach to a variety of different types of needleless connectors in a secure manner sufficient for preventing microbial ingress.

SUMMARY OF THE INVENTION

According to an aspect of the present disclosure, a disinfecting cap for a needleless connector includes an outer housing having a first end, an open second end, a sidewall extending between the first end and the second end, and at least one outer guide on an inner surface of the sidewall. The cap also includes an inner housing having a first end, an open second end sized to receive a distal end of the needleless connector, a sidewall extending between the first end and the second end, and at least one inner guide on an outer surface of the sidewall that interacts with the at least one outer guide of the outer housing. The cap also includes at least one absorbent member disposed in the inner housing configured to contain a cleaning solution for cleaning and/or disinfecting portions of the needleless connector engaged to the cap. Movement of the at least one inner guide relative to the at least one outer guide causes the inner housing to move axially into the outer housing and to alternate between rotating in a first direction and rotating in a second direction relative to the outer housing.

In accordance with an embodiment of the present invention, the inner housing is configured to move between an extended position, where the second end of the inner housing is outside of the outer housing, and a retracted position where the inner housing is entirely in the outer housing.

In accordance with an embodiment of the present invention, movement of the at least one inner guide relative to the at least one outer guide, as the inner housing moves from the extended position to the retracted position, causes the inner housing to rotate back-and-forth multiple times as the inner housing advances to the retracted position.

In accordance with an embodiment of the present invention, the inner housing rotates back-and-forth at least four times as the inner housing moves from an extended position to the retracted position.

In accordance with an embodiment of the present invention, when the distal end of the needleless connector is inserted into the inner housing, the inner housing rotates back-and-forth about the distal end of the needleless connector as the inner housing moves from an extended position to the retracted position.

In accordance with an embodiment of the present invention, first direction is a clockwise direction and the second direction is a counter-clockwise direction.

In accordance with an embodiment of the present invention, the needleless connector includes a female luer connector.

In accordance with an embodiment of the present invention, the cap is sized to receive female connectors having an outer diameter of from about 8.0 mm to about 14.0 mm and threads with a width at a crest of from about 0.3 mm to about 1.0 mm and a width at a root of the crest from about 0.5 mm to 1.2 mm.

In accordance with an embodiment of the present invention, the female luer connector includes a tubular body defining a tapered cavity; a septum covering an opening of the tubular body; and an external thread extending radially outward from an outer surface of the tubular body, wherein, when the female luer connector is inserted in the cap, the at least one absorbent member is configured to contact the outer surface, external thread, and septum of the female luer connector.

In accordance with an embodiment of the present invention, the at least one outer guide includes a track extending inwardly from the inner surface of the sidewall of the outer housing, and wherein the track comprises alternating segments for rotation in the first direction connected in series with segments for rotation in the second direction.

In accordance with an embodiment of the present invention, the track includes a groove or slot extending into the sidewall of the outer housing.

In accordance with an embodiment of the present invention, the at least one inner guide includes a protrusion extending radially outward from an outer surface of the sidewall of the inner housing received within the track of the outer housing.

In accordance with an embodiment of the present invention, the track further includes a longitudinally extending groove or slot extending between the open second end of the outer housing and a distal end of one of the of segments of the track positioned to receive the at least one inner guide as the inner housing is inserted into the outer housing.

In accordance with an embodiment of the present invention, the segments of the track are non-helical extending about the inner surface of the outer housing by less than a full rotation.

In accordance with an embodiment of the present invention, wherein each alternating segment causes the inner housing to rotate by an angular distance of from about 4 degrees to about 45 degrees about a longitudinal axis of the inner housing.

In accordance with an embodiment of the present invention, the rotation of the inner housing about the needleless connector inserted into the inner housing causes the at least one absorbent member to scrub the needleless connector inserted in the inner housing.

In accordance with an embodiment of the present invention, the inner housing forms an interference and/or friction engagement with the needleless connector which secures the inner housing to the needleless connector.

In accordance with an embodiment of the present invention, the at least one outer guide includes a first track and a separate second track on opposite sides of the inner surface of the sidewall of the outer housing, and wherein the first track is symmetrical with the second track about a longitudinal axis of the outer housing.

In accordance with an embodiment of the present invention, the at least one inner guide includes a first protrusion extending from an outer surface of the sidewall of the inner housing received within the first track and a second protrusion extending from the outer surface of the sidewall of the inner housing received within the second track of the outer housing.

In accordance with an embodiment of the present invention, the inner housing and/or the outer housing including a thermoplastic polymer material, such as polyester, polycarbonate, polypropylene, polyethylene, polyethylene terephthalate, or acrylonitrile butadiene styrene.

In accordance with an embodiment of the present invention, the outer housing further includes at least one tab that is pressed to a recessed position when the inner housing is in an extended position and which moves to a blocking position preventing removal of the inner housing from the outer housing, when the inner housing is inserted into the outer housing moving towards a retracted position.

In accordance with an embodiment of the present invention, the at least one tab is pivotally connected to the inner surface of the sidewall of the outer housing and biased to pivot away from the inner surface of the sidewall to the blocking position.

In accordance with an embodiment of the present invention, the outer housing includes a plurality of tabs that are biased to a recessed position when the inner housing is in an extended position and which move to a blocking position preventing removal of the inner housing from the outer housing, when the inner housing is inserted into the outer housing moving towards a retracted position.

In accordance with an embodiment of the present invention, the plurality of tabs include a plurality of elongated members having a first end connected to the sidewall of the outer housing and a second end configured to protrude into a space defined by the sidewall of the outer housing for blocking removal of the inner housing from the outer housing.

In accordance with an embodiment of the present invention, the at least one tab moves automatically from the recessed position to the blocking position upon insertion of the inner housing into the outer housing.

In accordance with an embodiment of the present invention, the at least one absorbent member is a cylinder having a circular first end, a circular second end, and a cylindrical sidewall extending therebetween.

In accordance with an embodiment of the present invention, the at least one absorbent member includes a sponge.

In accordance with an embodiment of the present invention, the at least one absorbent member includes an open cell foam, such as a porous foam having a thermoplastic elastomer.

In accordance with an embodiment of the present invention, the cleaning solution is absorbed by the at least one absorbent member.

In accordance with an embodiment of the present invention, the cleaning solution includes Isopropyl Alcohol (IPA).

In accordance with an embodiment of the present invention, the cleaning solution includes from about 0.5% to about 3.5% chlorhexidine gluconate and about 70% IPA In accordance with an embodiment of the present invention, a protective covers over the open second end of the inner housing for sealing the inner housing preventing contamination of the at least one absorbent member and/or evaporation of the cleaning solution absorbed by the at least one absorbent member.

In accordance with an embodiment of the present invention, the protective cover is attached to the inner housing by heat sealing.

In accordance with an embodiment of the present invention, a removable clamp is configured to be connected to an outer surface of the inner housing when the inner housing is in an extended position, which prevents insertion of the inner housing into the outer housing until the clamp is removed from the outer surface of the inner housing.

In accordance with an embodiment of the present invention, the removable clamp includes a C-clamp configured to grasp and engage the outer surface of the inner housing.

In accordance with an embodiment of the present invention, the removable clamp further includes a handle extending from the C-clamp for manipulating the removable clamp.

According to another aspect of the present disclosure, a manufacturing method for the disinfecting cap, as previously described, includes: forming a first part of the outer housing in a first mold; forming a second part of the outer housing in a second mold; attaching the first part to the second part by ultrasonic welding to form the outer housing, forming the inner housing by a single molding process, inserting the at least one absorbent member into the inner housing, and inserting the inner housing into the formed outer housing.

According to another aspect of the present disclosure, a method of use for the disinfecting cap, as previously described, includes: inserting a distal end of the needleless connector into the open second end of the inner housing, such that a surface of the absorbent member contacts the distal end of the needleless connector; and pressing the outer housing toward the needleless connector causing the inner housing to rotate relative to the outer housing and to the needleless connector for scrubbing surfaces of the needleless connector.

In accordance with an embodiment of the present invention, a method of using the cap of any includes inserting a distal end of the needleless connector into the open second end of the inner housing, such that a surface of the absorbent member contacts the distal end of the needleless connector, and pressing the outer housing toward the needleless connector causing the inner housing to rotate relative to the outer housing and to the needleless connector for scrubbing surfaces of the needleless connector.

In accordance with an embodiment of the present invention, the needleless connector is a female luer connector.

In accordance with an embodiment of the present invention, the method of using the cap further includes removing a protective cover positioned over the open second end of the inner housing from the inner housing prior to inserting the distal end of the needleless connector through the open second end of the inner housing.

BRIEF DESCRIPTION OF THE DRAWINGS

FIG. 6A is a perspective view of an outer housing of the disinfecting cap of FIG. 2A, according to an aspect of the present disclosure.

FIG. 6B is a perspective view of a cross-section of the outer housing of FIG. 6A.

FIG. 6C is a front view of a portion of the outer housing of FIG. 6A showing the tabs deployed to prevent removal of the inner housing from the outer housing, according to an aspect of the present disclosure.

DESCRIPTION OF THE INVENTION

Figure 1B:
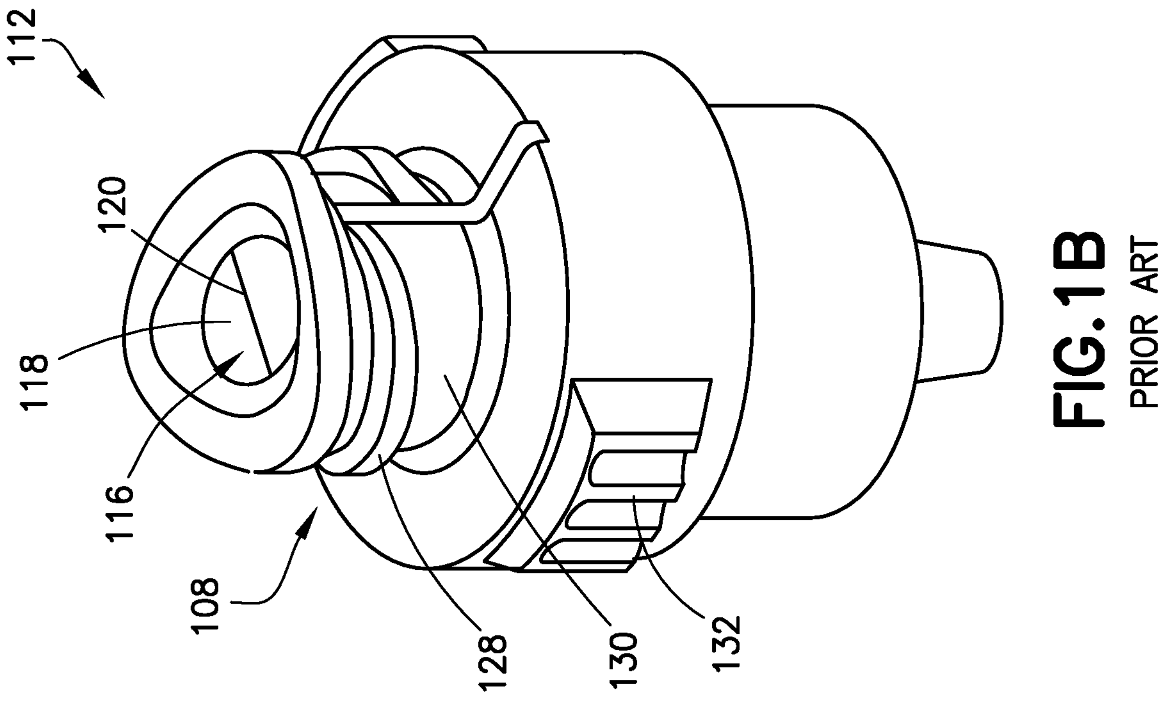
FIG. 1B is an example of a closed female connector including a septum with a slit, as is known in the prior art.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a cap 10 configured to be connected to a medical connector, such as to a male needleless connector 110 and/or to a female needleless connector 112, by a medical practitioner to prevent the connector 110, 112 from being contaminated by, for example, microorganisms, debris, or other contaminants. In some examples, the connector 110, 112 can be an access hub, port, or valve for a VAD. In other examples, the connector 110, 112 can be a component of another medical device, such as a fluid delivery device, syringe, catheter hub, or another medical device, as is known in the art. The medical practitioner using the cap 10 and connector 110, 112 can be a clinician or healthcare worker that performs fluid delivery or infusion procedures for patients. In particular, the "healthcare worker" can be a medical professional, such as a medical technician or nurse, trained to perform the medical procedure in accordance with sterile practices and protocols of a medical facility.

The cap 10 of the present disclosure is configured to clean and disinfect portions of the connector 110, 112, ensuring that the connector 110, 112 remains sterile prior to use. As used herein, cleaning a connector 110, 112 refers to exposing surfaces of the connector 110, 112 to a cleaning or disinfecting solution that destroys biological material (e.g., microorganisms and cells), as well to actions that mechanically remove particles (e.g., dust, dirt, microorganisms, cells, and other debris) from surfaces of the connector 110, 112, which can be referred to as "scrubbing" the connector 110, 112. The cap 10 of the present disclosure can also include features that encourage the practitioner to use the cap 10 to scrub surfaces of the connector 110, 112 in an appropriate manner. For example, as described in further detail herein, the cap 10 can include features that encourage the practitioner to twist the cap back-and-forth multiple times over a distal end of the connector 110, 112, thereby mechanically removing particles from surfaces of the connector 110, 112. After scrubbing is completed, the cap 10 can be configured to remain in place on the connector 110, 112 or port for up to seven days, which is a maximum time of recommended use permitted by many medical facility sterile practice guidelines. Once removed from the connector 110, 112, the cap 10 can include features that prevent reuse of the cap 10 and/or which provide a visual indication for the practitioner identifying that the cap 10 has already been used and should not be used again.

Male and Female Medical Connectors

The cap 10 of the present disclosure can be a universal cap meaning that it is configured to engage with or be connected to different sizes, configurations, and/or types of medical connectors. In particular, the cap 10 can be configured to engage with or be connected to a female connector 112. In some examples, the cap 10 can also be adapted or modified to be connected to a male connector 110.

Figure 1A:
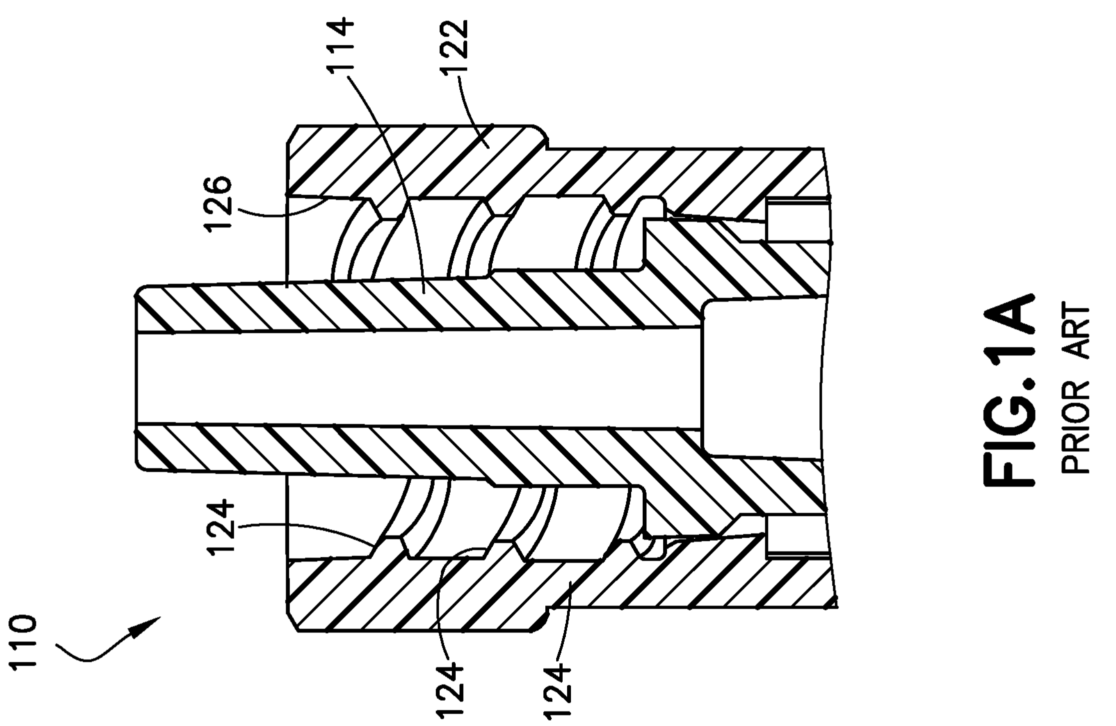
FIG. 1A is a cross-sectional view of an exemplary male connector, as is known in the prior art.

As used herein, a "male connector" refers to a connector 110 comprising an elongated member, such as a tubular member or stem 114, configured to be inserted in a tube or opening having an inner diameter that is larger than an outermost diameter of the male connector 110. An exemplary male connector 110 is shown in FIG. 1A. By contrast, a "female connector" refers to a connector 112 comprising an opening or port 116 that is configured to receive an elongated member or tubular member of another object or device in order to connect the object or device to the female connector 112. The female connector 112 can comprise an elongated distal end portion 108 with a cover or septum 118 over the opening 116. An exemplary female connector 112 including a septum 118 with a slit 120 is shown in FIG. 1B.

In some examples, the cap 10 is configured to engage different types of luer connectors, such as both a male luer connector 110 and a female luer connector 112. For example, the cap 10 can be an appropriate size to receive a female luer connector 112 having an outer diameter of about 7.0 mm to about 10.0 mm.

As used herein, a "luer connector" refers to a connector that includes a tapered portion (e.g., a luer taper) for creating a friction engagement between a tapered stem 114 or elongated member of a male luer connector 110 and a tapered cavity. For example, the male luer connector 110 can include a tapered stem 114 or elongated member having a tapered outer surface. The female luer connector 112 can include a tapered cavity configured to receive and engage the tapered stem 114 or elongated member to connect the male luer connector 110 to the female luer connector 112.

In some examples, the male connector 110 and the female connector 112 can include engaging structures, such as threads, for drawing the connector 110, 112 to another connector or port. For example, as shown in FIG. 1A, the male luer connector 110 can include an annular shield 122 or collar extending about the tapered stem 114 or elongated member. The annular shield 122 can include threads 124 on an inner surface 126 of the annular shield 122 configured to engage corresponding threads 128 on an outer surface 130 of the female luer connector 112. As shown in FIG. 1B, the female luer connector 112 includes the corresponding threads 128 extending from the outer surface 130 positioned to engage the threads 124 on the inner surface 126 of the annular shield 122 of the male luer connector 110. Twisting the female connector 112 relative to the male connector 110 causes the corresponding threads 128 to engage, which draws the connectors 110, 112 together, such that the tapered stem 114 or elongated member of the male luer connector 110 moves through the opening 116 of the female connector 112. In some examples, the female connector 112 can also include vertical ribs 132 near a proximal end of the female connector 112, which can be used to manipulate the female connector 112 making it easier to twist the female connector 112 relative to another connector or device.

There are numerous commercially available medical devices, such as hubs, ports, and valves, which include different variations of male or female connectors 110, 112, such as male and female luer connectors. As described in further detail herein, the cap 10 of the present disclosure can be adapted to connect to different types and sizes of needleless connectors 110, 112. For example, the cap 10 can be configured to attach to luer connectors, such as male or female Luer-Lok™ connectors by Becton, Dickinson and Company. The cap 10 can also be configured to cover different connector designs including, without limitation, the BD Q-Syte™, BD MaxZero™, BD MaxPlus™, and SmartSite™ needle free connectors by Becton, Dickinson and Company. The cap 10 can also be configured to be connected to male or female connectors by other manufactures including, without limitation, MicroClave® connectors (ICU Medical Inc.) and Ultrasite® connectors (B. Braun Medical Inc.).

Disinfecting Cap for Needleless Connectors

FIGS. 2A-6C illustrate an exemplary disinfecting cap 10 configured to engage a needleless connector, such as the previously described male connector 110 or female connector 112. The cap 10 includes a multi-part housing that both engages and cleans surfaces of the connector 110, 112 ensuring that the connector 110, 112 remains sterile and ready for use. Specifically, the cap 10 comprises an outer housing 12 and an inner housing 14 that retracts into the outer housing 12 as the cap 10 is secured to the needleless connector 110, 112. The cap 10 also includes an absorbent member 16 disposed in the inner housing 14 that contacts surfaces of the needleless connector 110, 112 for cleaning and/or disinfecting the surfaces of the needleless connector 110, 112.

As described in further detail herein, the inner housing 14 is configured to twist or rotate relative to the outer housing 12 and to the female connector 110, 112 inserted into the inner housing 14 as the inner housing 14 retracts into the outer housing 12. Twisting or rotating of the inner housing 14 relative to the connector 110, 112 causes the absorbent member 16 to contact and rub against surfaces of the connector 110, 112 for mechanically removing (e.g., scrubbing) particles from surfaces of the connector 110, 112. In particular, the cap 10 of the present disclosure can be configured to sweep across or twist or rotate back-and-forth over surfaces of the connector 110, 112 a number of times (e.g., at least four or more sweeps) during insertion of the inner housing 14 into the outer housing 12. The number of sweeps, or back-and-forth rotations, can be selected to satisfy requirements for cleaning, disinfecting, and sterilizing connectors 110, 112 that have been adopted by many medical facilities. Accordingly, using the caps 10 disclosed herein encourages practitioners to clean connectors 110, 112 in a manner that complies with accepted or required cleaning and sterilization protocols.

As shown in FIGS. 2A-3C, as well as FIGS. 5A-6C, the outer housing 12 is a container, such as a cup-shaped part, comprising a first or top end 18, an open second or bottom end 20, and a sidewall 22 extending between the top end 18 and the bottom end 20. In some examples, the top end 18 of the outer housing 12 is a closed structure for retaining the inner housing 14, absorbent member 16, and cleaning solution contained by the absorbent member 16 within the outer housing 12. In some examples, the top end 18 could be open and covered by a separate and/or removable cap, cover, seal, or similar article. The sidewall 22 of the outer housing 12 is generally cylindrical having a cylindrical outer surface 24 and a cylindrical inner surface 26 defining a cylindrical cavity sized to receive the inner housing 14. In some examples, portions of the outer surface 24 and/or the inner surface 26 of the outer housing 12 can also be sloped, angled, or tapered, so that it is easier to insert the inner housing 14 and/or connector 110, 112 into the outer housing 12.

The outer housing 12 further comprises one or more guiding surfaces, members, or structures (referred to herein as an outer guide 28) on the inner surface 26 of the sidewall 22. In some examples, the outer guide 28 can be a track including, for example, slots, ridges, grooves, or similar protruding or recessed structures that define a path for movement of the inner housing 14 through the outer housing 12 and/or relative to other portions of the cap 10 and connector 110, 112 connected thereto. As described in further detail herein, the outer guide 28 is configured or shaped to cause the inner housing 14 to twist, rotate, or sweep over surfaces of the connector 110, 112 multiple times for mechanically removing (e.g., scrubbing) particles from the connector 110, 112.

The cap 10 further comprises the inner housing 14, which is inserted into the outer housing 12. Specifically, the inner housing 14 is configured to move into the outer housing 12 from an initial or extended position (shown in FIGS. 2A and 3A), in which a bottom end 30 of the inner housing 14 extends beyond the bottom end 20 of the outer housing 12 to a final or retracted position (shown in FIGS. 2B and 3C), in which the inner housing 14 is entirely enclosed within the outer housing 12. As shown in FIGS. 2A-4C, the inner housing 14 can comprise a first or top end 32 (which can be open, closed, or covered by a removable cap or cover), the open bottom end 30 sized to receive a distal end of the female needleless connector 112, and a sidewall 34 extending between the top end 32 and the bottom end 30. The inner housing 14 also includes an inner guide 36 on an outer surface 38 of the sidewall 34. The inner guide 36 is shaped and positioned to be received by the outer guide 28 of the outer housing 12 for guiding movement of the inner housing 14 relative to the outer housing 12. For example, the inner guide 36 can be a protrusion, such as a pin, post, dowel, elongated member, or similar structure, extending from the outer surface 38 of the sidewall 34 of the inner housing 14. The inner guide 36 can be positioned to be received by and slide through the outer guide 28, thereby guiding the movement and particularly rotation of the inner housing 14 relative to the outer housing 12 and connector 110, 112 as the inner housing 14 is inserted into the outer housing 12.

Figures 4A, 4B, 4C:
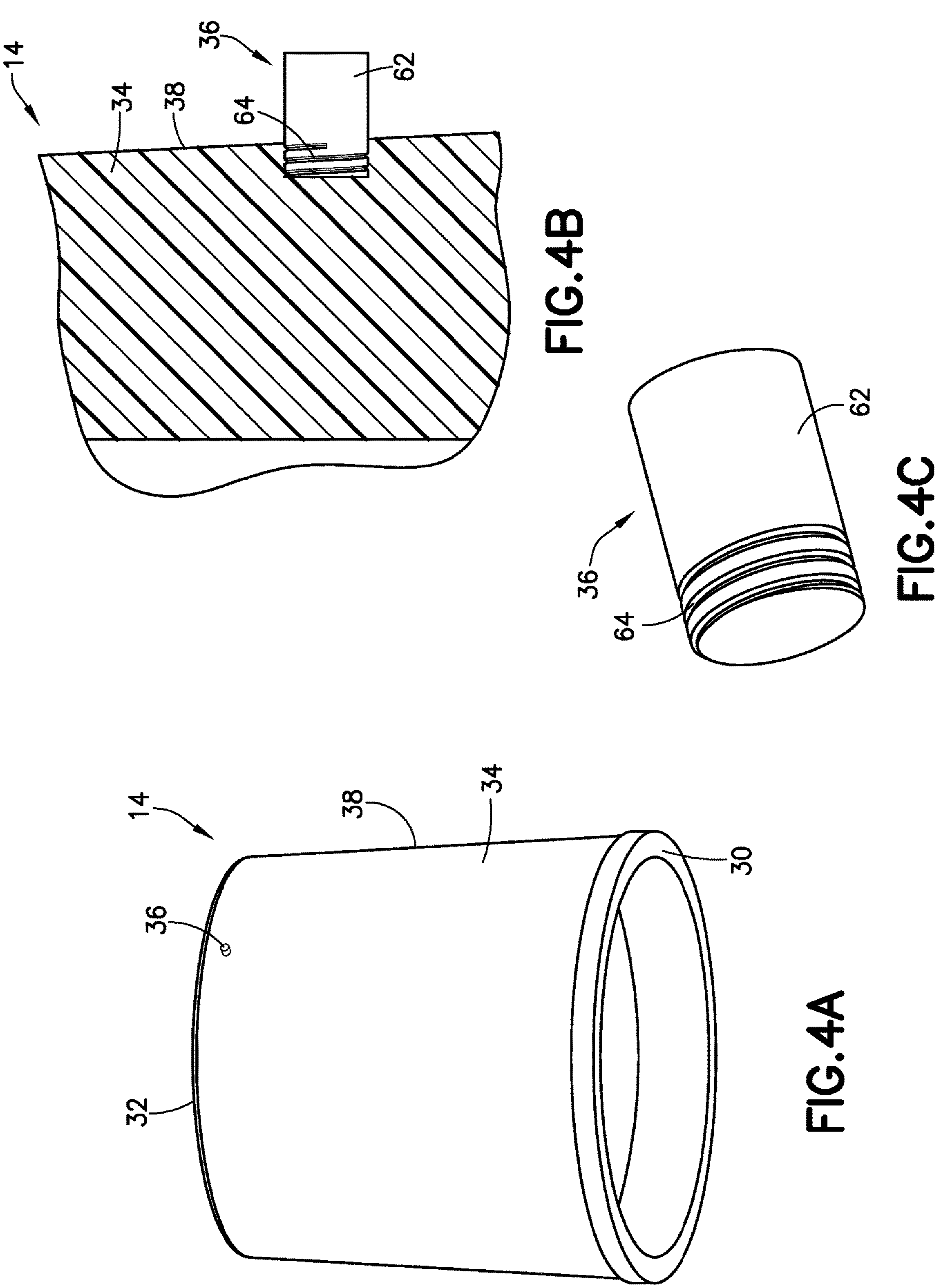
FIG. 4A is a perspective view of an inner housing of the disinfecting cap of FIG. 2A showing the open bottom end of the inner housing, according to an aspect of the present disclosure.
FIGS. 4B and 4C are schematic drawings showing a pin of the inner housing of FIG. 4A, according to an aspect of the present disclosure.

In some examples, the inner guide 36 can be a pin or post that is integrally formed with and extends from the sidewall 34 of the inner housing 14. In other examples, as shown in FIGS. 4B and 4C, the inner guide 36 can be a threaded pin 62 including threads 64. The threaded pin 62 can be inserted into a corresponding cavity or depression in the sidewall 34 of the inner housing 14 for engaging the threaded pin 62 to the inner housing 14.

The inner housing 14 is configured to be connected to the needleless connector 110, 112 by inserting a distal end of the needleless connector 110, 112 through the open bottom end 30 of the inner housing 14. The inner housing 14 can form an interference and/or friction engagement with the needleless connector 110, 112, which secures the cap 10 to the needleless connector 110, 112. Because the inner housing 14 of the cap 10 engages the connector 110, 112 by a friction fit and does not directly engage threads of the connector 110, 112, the cap 10 can be used with connectors 110, 112 having a variety of thread patterns, sizes, and shapes.

Once the needleless connector 110, 112 is inserted into the inner housing 14, the inner housing 14 moves through the outer housing 12, thereby securing the needleless connector 110, 112 to the cap 10. As previously described, the guides (e.g., the outer guide 28 of the outer housing 12 and the inner guide 36 of the inner housing 14) are positioned to guide movement of the inner housing 14 as it is being inserted into the outer housing 12. Specifically, as the inner housing 14 is inserted into the outer housing 12 (as shown by arrow A2 in FIG. 3A), the inner guide 36 moves along the outer guide 28, which causes the inner housing 14 to move axially into the outer housing 12. The positioning of the guides 28, 36 also causes the inner housing 14 to alternate between twisting or rotating in a first or clockwise direction (shown by arrow A2 in FIG. 3B) and twisting or rotating in a second or counterclockwise direction (shown by arrow A3 in FIG. 3B) relative to the outer housing 12 and connector 110, 112. In order to provide the twisting or back-and-forth rotation, as shown most clearly in FIGS. 3A-3C, the outer guide 28 or track includes portions or segments 40 that cause the inner housing 14 to rotate in the clockwise direction alternating with other portions or segments 42 that cause the inner housing 14 to rotate in a counter-clockwise direction. Specifically, as shown in FIGS. 3A-3C, the track or the outer guide 28 includes four clockwise segments 40 and four counterclockwise segments 42, meaning that the inner housing 14 alternates between rotating in the clockwise and the counterclockwise directions four times as the inner housing

Figure 2A:
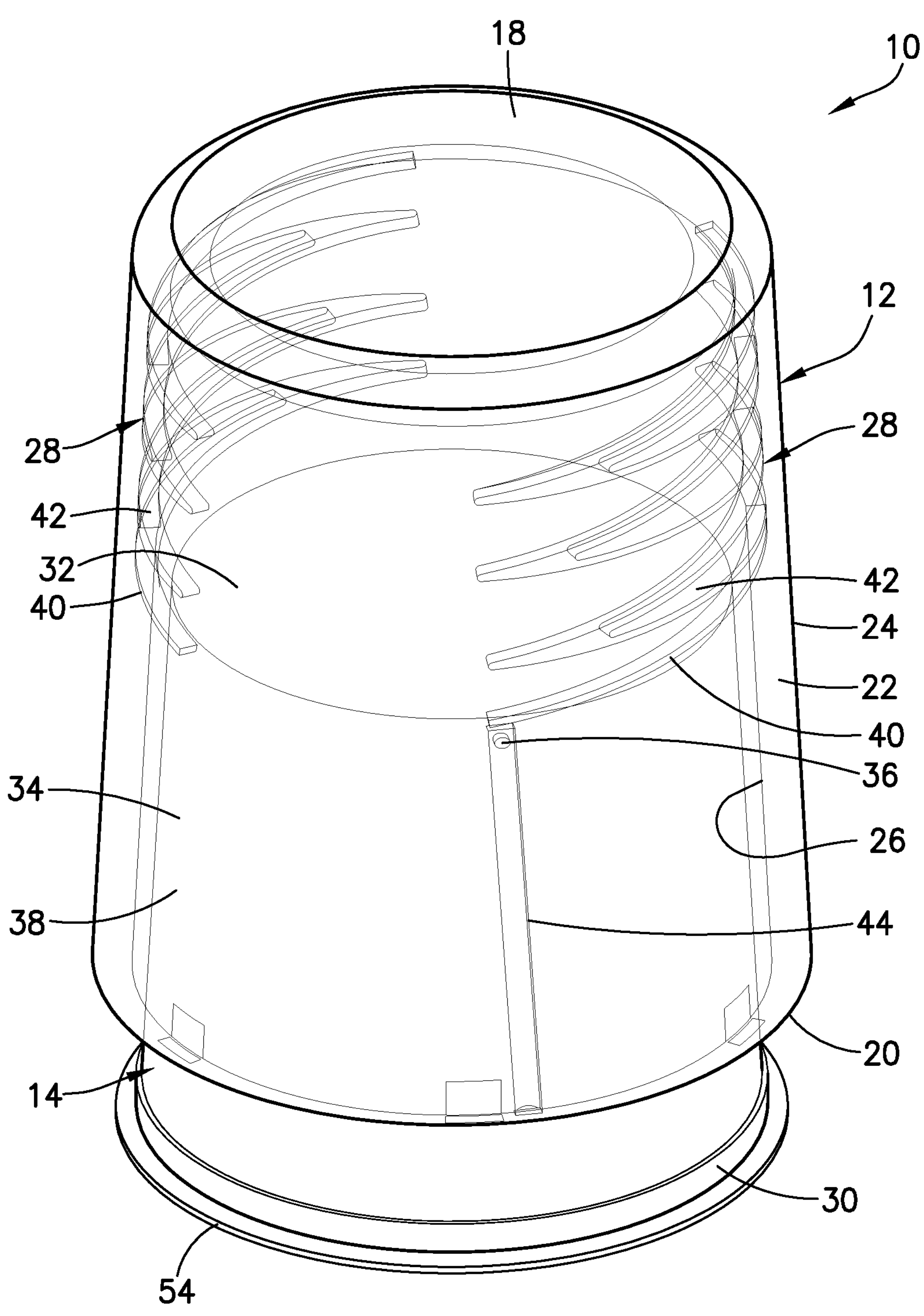
FIG. 2A is a perspective view of a disinfecting cap for a needleless connector in an initial or extended position, according to an aspect of the present disclosure.
Figure 2B:
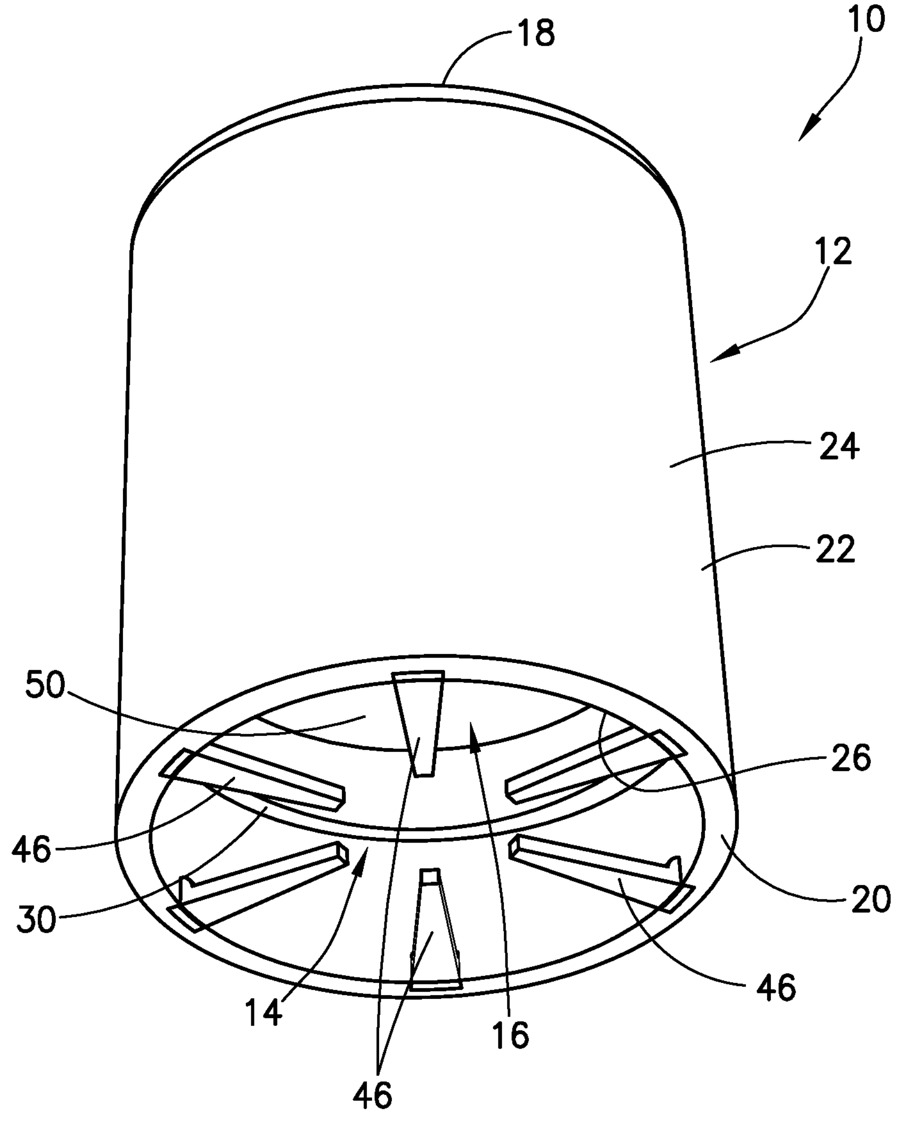
FIG. 2B is another perspective view of the disinfecting cap of FIG. 2A showing an open bottom portion of the cap in a final or retracted position, according to an aspect of the present disclosure.
Figure 2C:
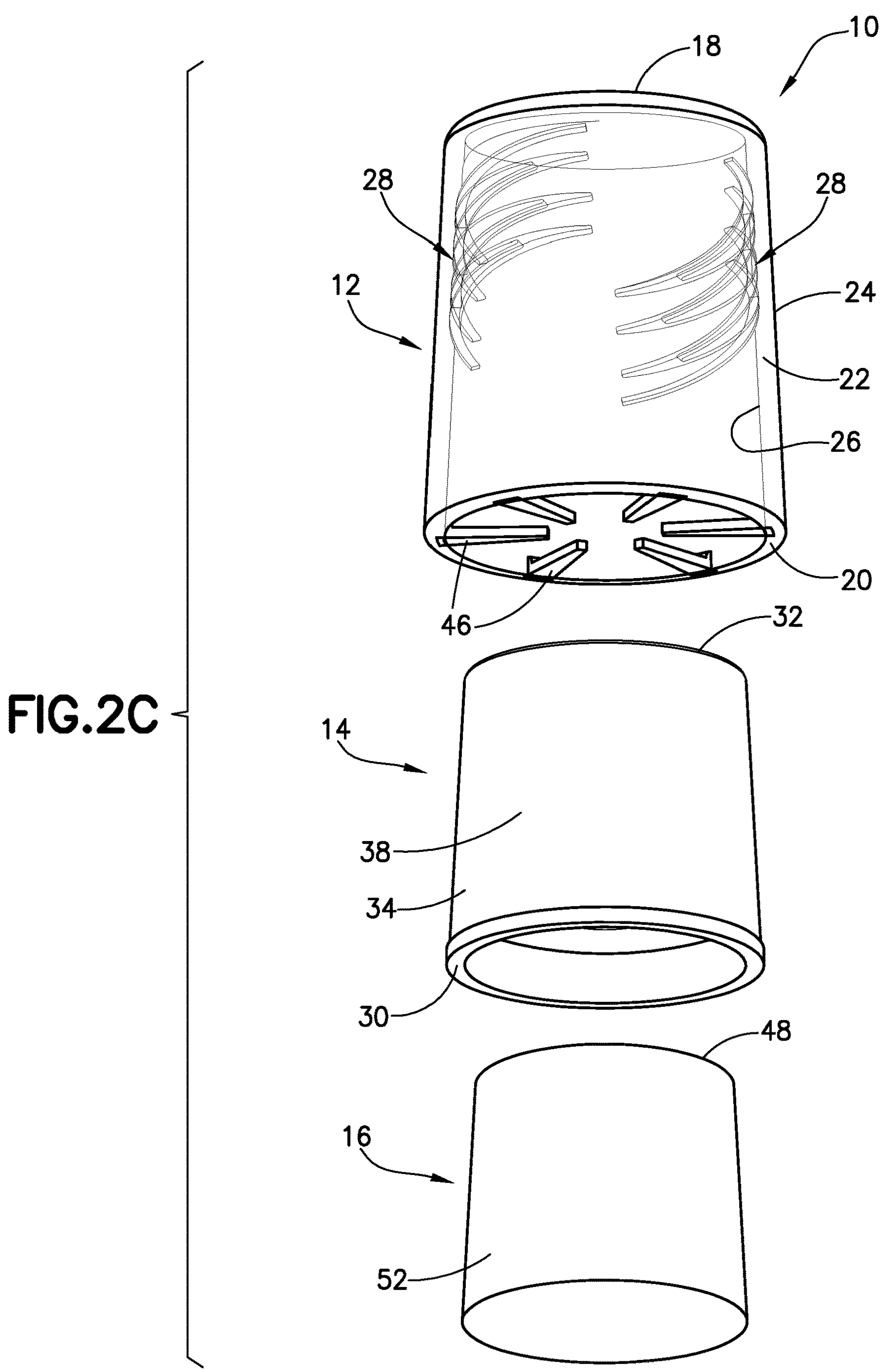
FIG. 2C is an exploded view of the disinfecting cap of FIG. 2A.
Figures 3A, 3B, 3C:
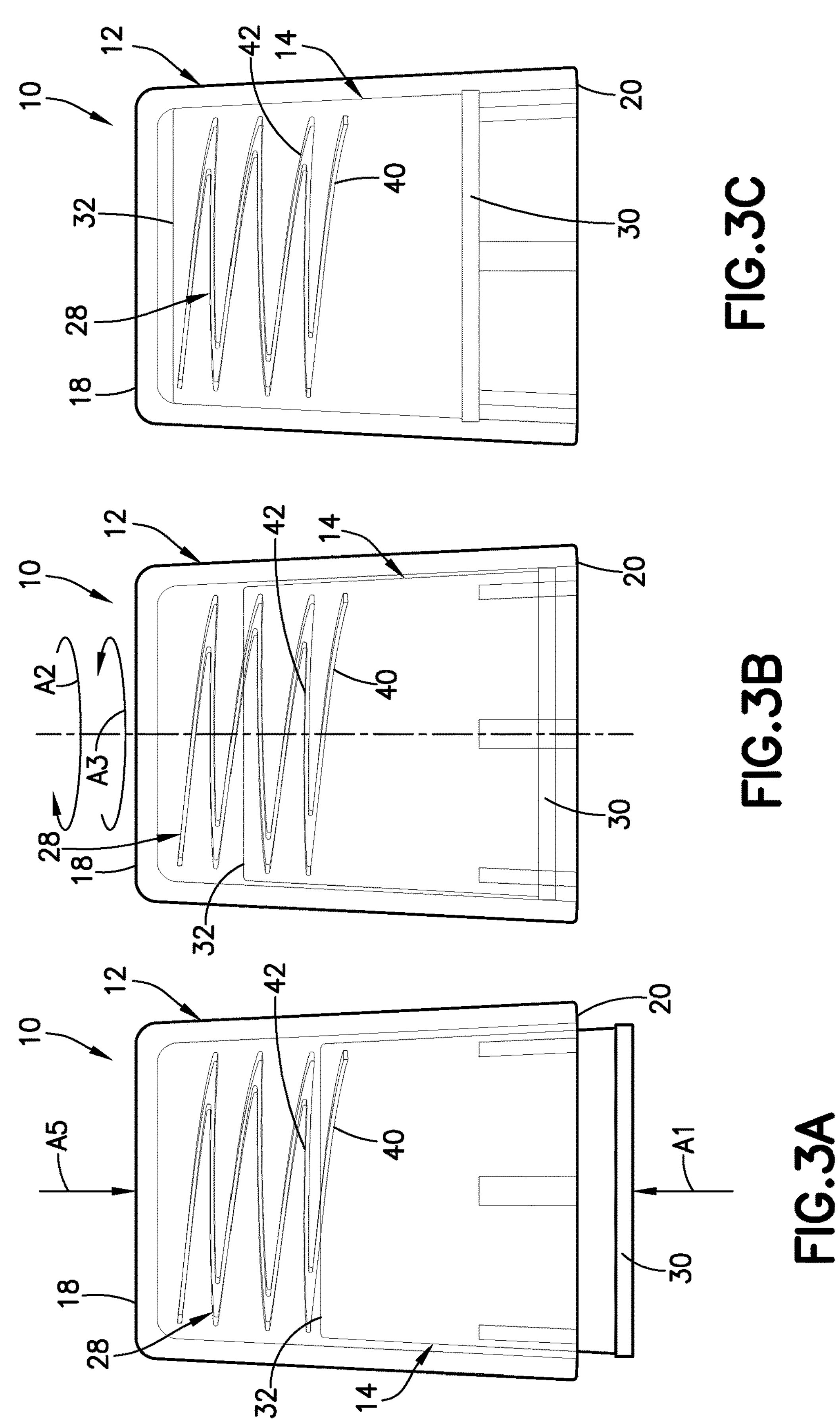
FIG. 3A is a front view of the disinfecting cap of FIG. 2A in the initial or extended position, according to an aspect of the present disclosure.
FIG. 3B is a front view of the disinfecting cap of FIG. 2A in an intermediate or in-use position.
FIG. 3C is a front view of the disinfecting cap of FIG. 2A in the final or retracted position.

14 moves from the extended position (shown in FIGS. 2A and 3A), through an intermediate or in-use position (shown in FIG. 3B), to the final or retracted position (shown in FIGS. 2B and 3C).

The angular distance or degree of each successive rotation or sweep is determined based on the configuration of the guides 28, 36. For example, the guides 28, 36 can be configured to cause the inner housing 14 to twist or rotate by an angular distance of from about 45 degrees to about 270 degrees in the clockwise direction (shown by arrow A2 in FIG. 3B) during each clockwise rotation or sweep. In a similar manner, the inner housing 14 can rotate by an angular distance of from about 45 degrees to about 270 degrees in the counterclockwise direction (shown by arrow A3 in FIG. 3B) during each counterclockwise rotation or sweep.

The back-and-forth (e.g., clockwise and counterclockwise) twisting or rotation of the inner housing 14 relative to the outer housing 12 and to the needleless connector 110, 112 causes the absorbent member 16 to rub against surfaces of the needleless connector 110, 112, thereby mechanically removing (e.g., scrubbing) the particles, such as dust, dirt, debris, microorganisms, bacteria, cells, and any other contaminates from surfaces of the needleless connector 110, 112.

As previously discussed, the length and configuration of the outer guide 28 or track can be selected based on protocols or requirements for disinfecting hubs or ports using disinfecting caps 10. For example, the outer guide 28 or track can include enough segments 40, 42 so that the cap 10 is rotated or sweeps over the connector 110, 112 a number of times required by a medical facility sterilization protocol. As shown in FIGS. 3A-3C, the outer guide 28 includes four clockwise segments 40 and four counterclockwise segments 42 meaning that the cap 10 rotates or sweeps over the connector 110, 112 eight times as the inner housing 14 retracts into the outer housing 12. In other examples, the outer guide 28 can be made with fewer or more segments 40, 42 depending upon requirements of a particular medical facility or sterilization protocol. Also, the outer guide 28 or track can be long enough to ensure that the practitioner continues to scrub the female connector 112 for a length of time or duration required or suggested by a medical facility sterilization protocol. For example, the outer guide 28 or track can be long enough to ensure that it takes at least 10 seconds, 20 seconds, 30 seconds, or longer to move the inner housing 14 from the extended position to the retracted position to comply with a particular sterilization protocol.

In addition to the segments 40, 42 that guide rotation of the inner housing 14 in the clockwise and counter-clockwise directions, the outer guide 28 can also include a longitudinal or vertical slot 44 or groove positioned for initially inserting the inner guide 36 into the outer guide 28 or track. For example, the vertical slot 44 can extend between the open bottom end 20 of the outer housing 12 and a distal or bottom end of one of the segments 40, 42 of the track positioned to receive the inner guide 36 as the inner housing 14 is inserted into the outer housing 12.

In some examples, the housings 12, 14 can include multiple separate guiding structures or guides 28, 36 for improving stability of the inner housing 14. For example, as shown most clearly in FIG. 2A, the outer housing 12 can include two separate guides 28 or tracks, each of which is positioned to receive a separate inner guide 36, such as a protrusion or pin, extending from the inner housing 14. In particular, the inner housing 14 can include a first protrusion or pin configured to be received within a first guide 28 or track and a separate second protrusion or pin configured to be received within a second guide 28 or track on opposite sides of the inner surface 26 of the sidewall 22 from the first guide 28 or track. In some examples, the first guide 28 or track can be symmetrical with the second guide 28 or track about a longitudinal axis of the outer housing 12. Including multiple tracks 28 and protrusions can increase stability of the inner housing 14, ensuring that the inner housing 14 moves smoothly into the outer housing 12 and rotates relative to the outer housing 14 for scrubbing the female connector 112.

With specific reference to 2A, 2B, and 6A-6C, in some examples, the outer housing 12 further comprises tabs 46, such as blocking or interference tabs, positioned to prevent removal of the inner housing 14 from the outer housing 12 and to provide visual feedback showing the practitioner that a cap 10 has already been used and should be discarded. In particular, the tabs 46 can be configured to move automatically to an extended or blocking position when the inner housing 14 is inserted into the outer housing 12 to show practitioners that the cap 10 has been used.

As shown most clearly in FIG. 6A, the outer housing 12 includes six generally triangular shaped tabs 46 positioned equidistantly about a circumference of the inner surface 26 of the sidewall 22 of the outer housing 12. However, the shape, number, and orientation of the tabs 46 is not intended to be limiting for the present disclosure. In some examples, the outer housing 12 can include fewer than six tabs 46 or more than six tabs 46. Also, the tabs 46 can be rectangular, square-shaped, trapezoidal, or any other convenient shape suitable for blocking the inner housing 14 from being removed from the outer housing 12. As shown in FIGS. 6A-6C, the tabs 46 can be positioned proximate to the open bottom end 20 of the outer housing 12. The tabs 46 can be pivotally connected to the inner surface 26 of the sidewall 22 of the outer housing 12 and biased to pivot away from the inner surface 26 of the sidewall 22 toward a blocking position. The tabs 46 can initially be provided in a retracted or recessed position when the inner housing 14 is in an extended position pushing the tabs 46 away from the open bottom end 20 of the outer housing 12. As the inner housing 14 retracts into the outer housing 12, the tabs 46 move (in a direction shown by arrow A4 in FIG. 6C) from the retracted or recessed position to an extended or blocking position (shown in FIGS. 6A-6C).

The inner housing 14 and the outer housing 12 can be formed from plastic materials commonly used for disposable medical devices and accessories. For example, the inner housing 14 and/or the outer housing 12 can be formed from a thermoplastic polymer material, such as polyester, polycarbonate, polypropylene, polyethylene, polyethylene terephthalate, or acrylonitrile butadiene styrene. In some examples, the inner housing 14 and/or the outer housing 12 can be formed from a durable material, such as a material having a shore hardness "D" value of less than or equal to about 95. Alternatively, the inner housing 14 or the outer housing 12 can be formed from a more flexible material, such as a material having a shore hardness "A" value less than or equal to about 95. In particular, portions of the inner housing 14 may be made to be sufficiently flexible to bend or deform in order to engage or connect with female needleless connectors 112 of different shapes, sizes, and configurations.

The outer housing 12 and/or the inner housing 14 can include or can be formed from a single molded part or from multiple molded parts, such as molded parts made by injection molding or other common plastic molding processes, as are known in the art. If required, the multiple molded parts can be assembled together to form the outer housing 12 and/or the inner housing 14 by common assembly processes (e.g., ultrasonic welding, laser welding, adhesives, etc.) as are known in the art.

With reference again to FIGS. 2A-2C, the cap 10 further comprises the absorbent member 16, which is disposed in the inner housing 14, as shown in FIG. 2B. The absorbent member 16 can be a cylindrical or tubular structure having a circular top 48, a circular bottom 50, and a cylindrical outer surface 52 extending therebetween. The absorbent member 16 can be retained within a cylindrical cavity defined by the inner housing 14 by a friction engagement between surfaces of the absorbent member 16 and inner surfaces of the inner housing 14. Alternatively or in addition, the absorbent member 16 can be retained within the inner housing 14 by conventional fasteners or adhesives, as are known in the art.

The absorbent member 16 is generally formed from a deformable material that is capable of compressing, bending, and deforming as the connector 110, 112 is inserted into the inner housing 14. In particular, the absorbent member 16 can compress or deform to match a shape of outer surfaces of the needleless connector 110, 112 inserted into the inner housing 14. Accordingly, the absorbent member 16 can be configured to contact many portions of the outer surfaces of the connector 110, 112 in order to scrub or mechanically remove particles, dirt, dust, microbes, and other debris from surfaces of the connector 110, 112. Further, the absorbent member 16 can be formed from an abrasive and/or porous material that contacts surfaces of the connector 110, 112, providing enhanced scrubbing and particle removal from surfaces of the connector 110, 112 compared to materials that are softer, smoother, or less abrasive.

In some examples, the absorbent member 16 comprises or is formed from an absorbent material capable of absorbing the cleaning or disinfecting solution for cleaning and/or disinfecting portions of the connector 110, 112. Further, the absorbent member 16 can be configured to radially and/or axially compress as the distal portion of the connector 110, 112 is inserted into the inner housing 14. The radial and/or axial compression of the absorbent member 16 can cause the cleaning solution of the absorbent member 16 to flow away from the absorbent member 16 and to contact the threads and other surfaces of the connector 110, 112 for cleaning and disinfecting portions of the connector 110, 112.

In some examples, the absorbent member 16 can comprise a thermoplastic elastomer, such as polypropylene, polyethylene, or synthetic or natural rubber (e.g., isoprene). The absorbent member 16 can also comprise a porous foam (e.g., an open cell foam) or sponge capable of absorbing the cleaning or disinfecting solution, such as a foam or sponge comprising polyurethane. In other examples, the foam material can be a Plastazote® foam, which is an engineered polymer foam by Zotefoams PCL.

In some examples, the absorbent member 16 is provided (e.g., presoaked) with the cleaning or disinfecting solution during manufacturing of the cap 10. The cleaning or disinfecting solution can be an antimicrobial, anti-fungal, antibacterial, or antiviral solution that cleans and sterilizes surfaces of the connector 110, 112. In some examples, the cleaning solution can be isopropyl alcohol (IPA), such as about 70% IPA. In other examples, the cleaning solution can be about 0.5% to about 3.5% chlorhexidine gluconate in combination with about 70% IPA. A chlorohexidine composition may be beneficial because it has a slower evaporation rate than IPA and, therefore, can provide a more persistent disinfectant activity after the cap 10 is removed from the connector 110, 112 and before the VAD is connected to the hub, port, or valve.

In some examples, the cap 10 can further comprise a removable and/or disposable protective cover 54 (shown in FIG. 2A) positioned over the open bottom end 30 of the inner housing 14. The protective cover 54 can be provided to protect components and portions of the cap 10, such as the inner housing 14 and absorbent member 16, during transport and storage to prevent contamination and to prevent the cleaning or disinfecting solution from evaporating prior to use. The protective cover 54 can comprise a sheet, such as a polymer film, with adhesive on a first side of the sheet for removably mounting the protective cover 54 to the open bottom 30 of the inner housing 14. Alternatively, the protective cover 54 can be removably mounted to the open bottom 30 of the inner housing 14 by heat sealing. The protective cover 54 can be formed from a material that is impervious or substantially impervious to air, so that the cleaning or disinfecting solution on the absorbent member 16 does not evaporate or dry-out. Accordingly, the protective cover 54 can increase a shelf life of the cap 10, as well as prevent microbes and other debris from collecting in the cap 10 prior to use.

Figures 7A, 7B:
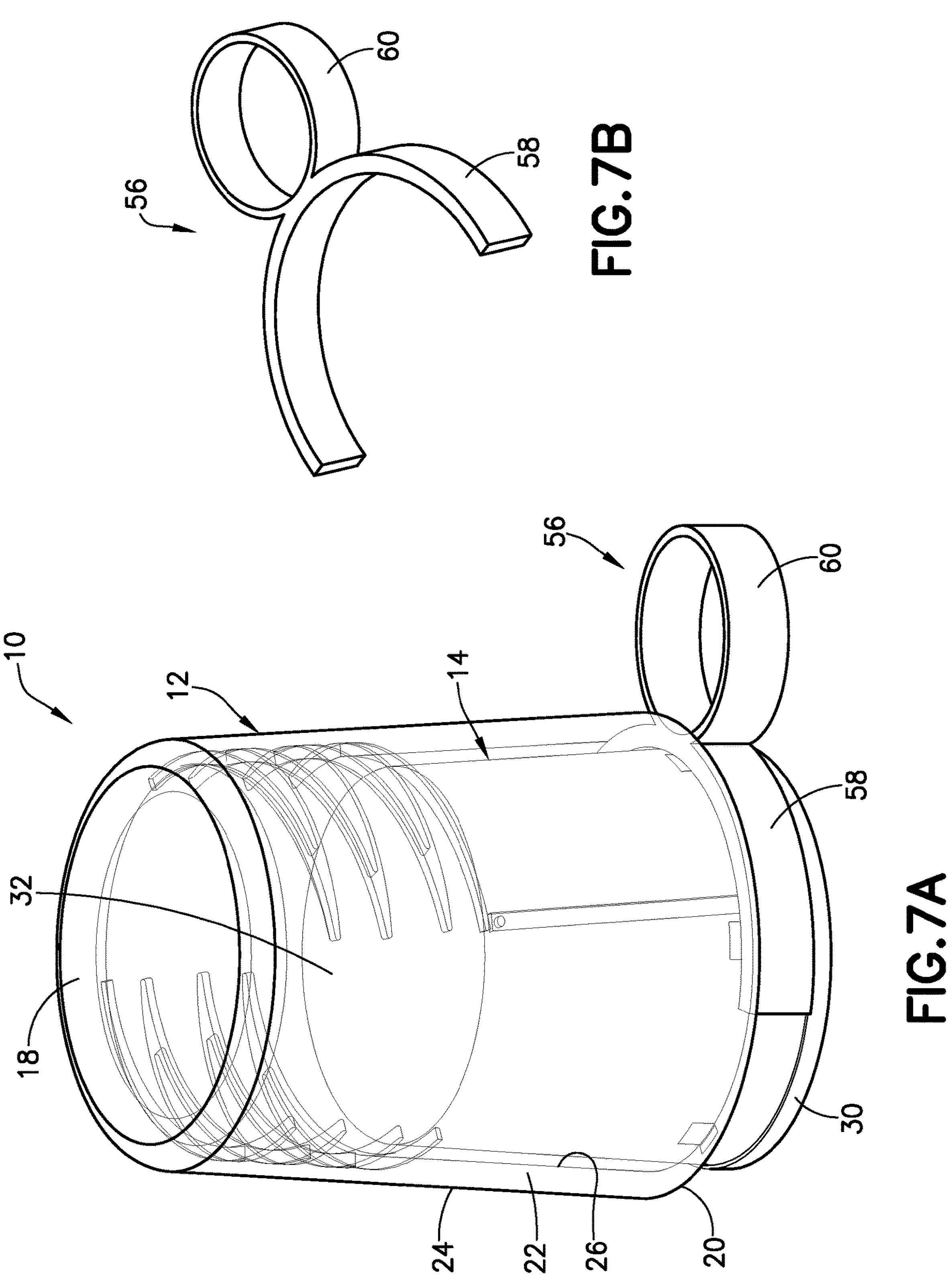
FIG. 7A is a perspective view of the disinfecting cap of FIG. 2A including a removable clamp engaged to the cap for maintaining the cap in the initial or extended position, according to an aspect of the present disclosure.
FIG. 7B is a perspective view of the removable clamp of FIG. 7A.

With reference to FIGS. 7A and 7B, in some examples, the cap 10 can also be provided with various retaining or locking structures for preventing components of the cap 10 from moving together or activating until the cap 10 is ready for use. For example, the cap 10 can include a removable clamp 56 configured to be connected to the cap 10 for preventing the inner housing 14 from being inserted into the outer housing 12 at unexpected or inappropriate times. As shown in FIG. 7A, the clamp 56 is connected to the outer surface 38 of the inner housing 14 when the inner housing 14 is in an extended position. For example, the clamp 56 can be held in place by a friction engagement with the outer surface 38 of the inner housing 14. The clamp 56 prevents insertion of the inner housing 14 into the outer housing 12 until the clamp 56 is removed from the inner housing 14. In some examples, the clamp 56 can be a molded structure, such as a molded part formed from a thermoplastic polymer resin by injection molding or another plastic molding process. In some examples, the removable clamp 56 can include a C-clamp portion 58 configured to grasp and engage the outer surface 38 of the inner housing 14 and a handle portion 60 or grip extending from the C-clamp portion 58. For example, as shown in FIGS. 7A and 7B, the handle 60 can be a circular segment extending from the C-clamp portion 58 configured to be grasped by the practitioner to remove the clamp 56 from the inner housing 14.

Method for Attaching a Connector to the Cap

Figure 5A:
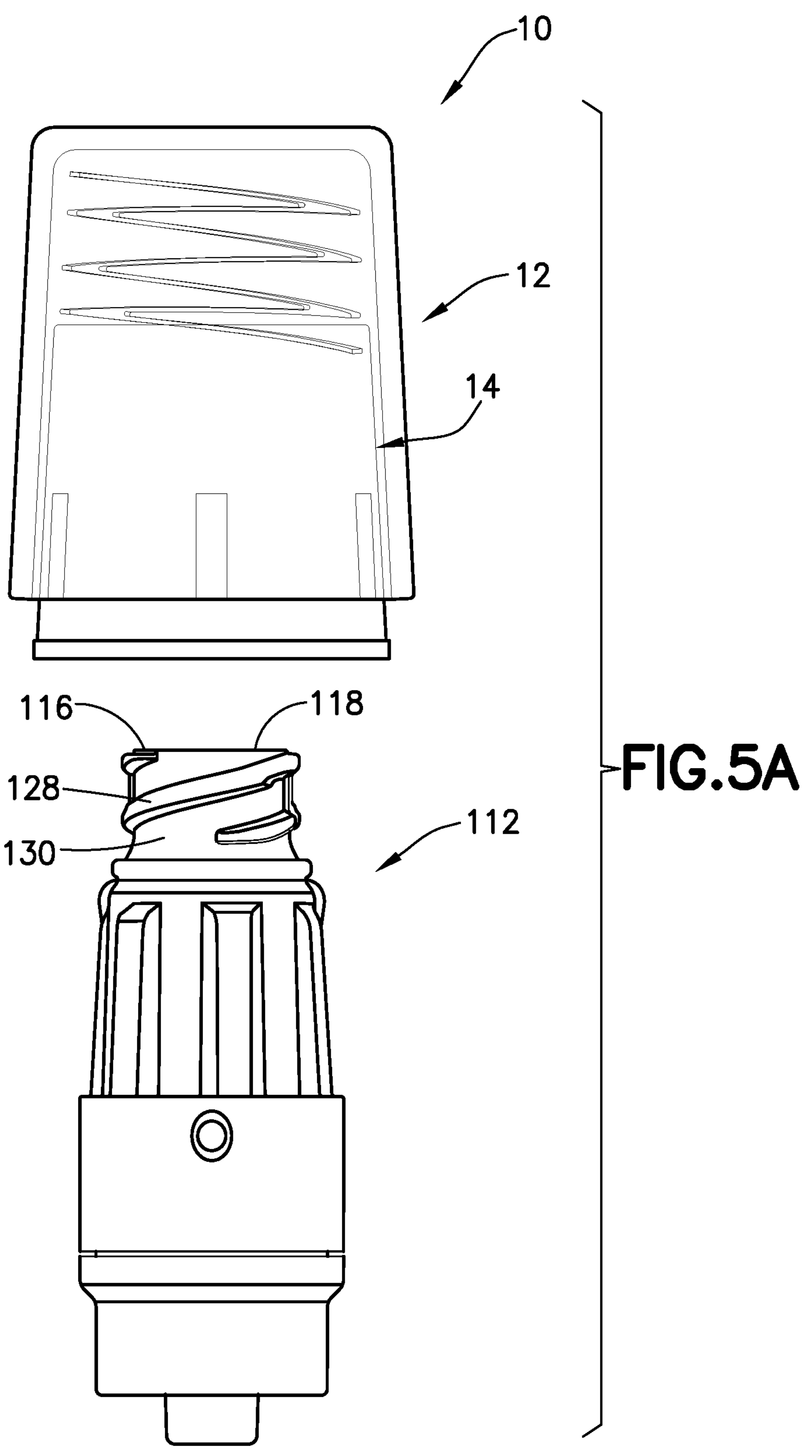
FIG. 5A is a front view showing the cap of FIG. 2A in an initial or extended position proximate to a female needleless connector, according to an aspect of the present disclosure.
Figure 5B:
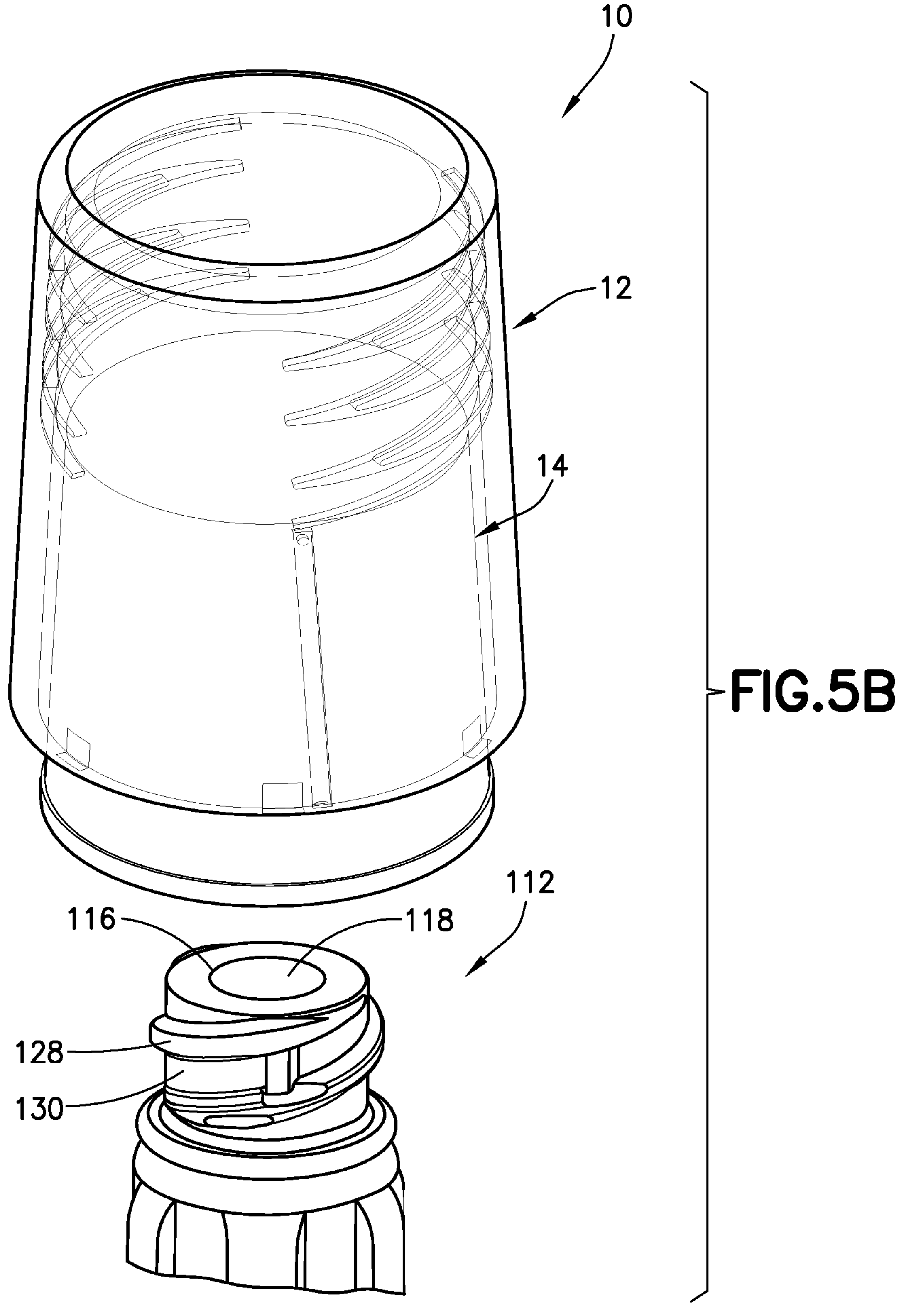
FIG. 5B is a perspective view showing the cap of FIG. 2A in the initial or extended position proximate to a female needleless connector of FIG. 5A.
Figure 5C:
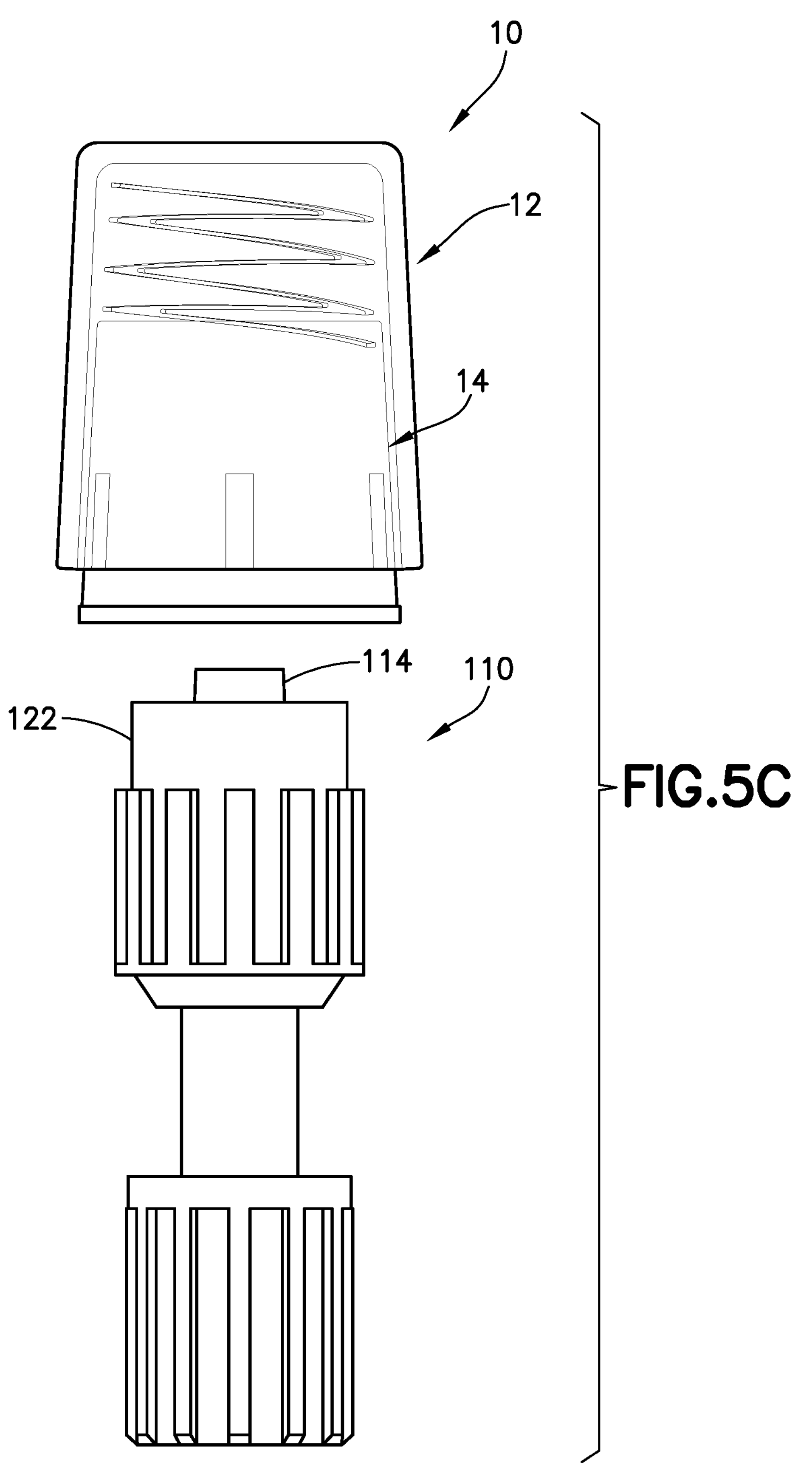
FIG. 5C is a front view showing the cap of FIG. 2A in an initial or extended position proximate to a male needleless connector, according to an aspect of the present disclosure.
Figure 5D:
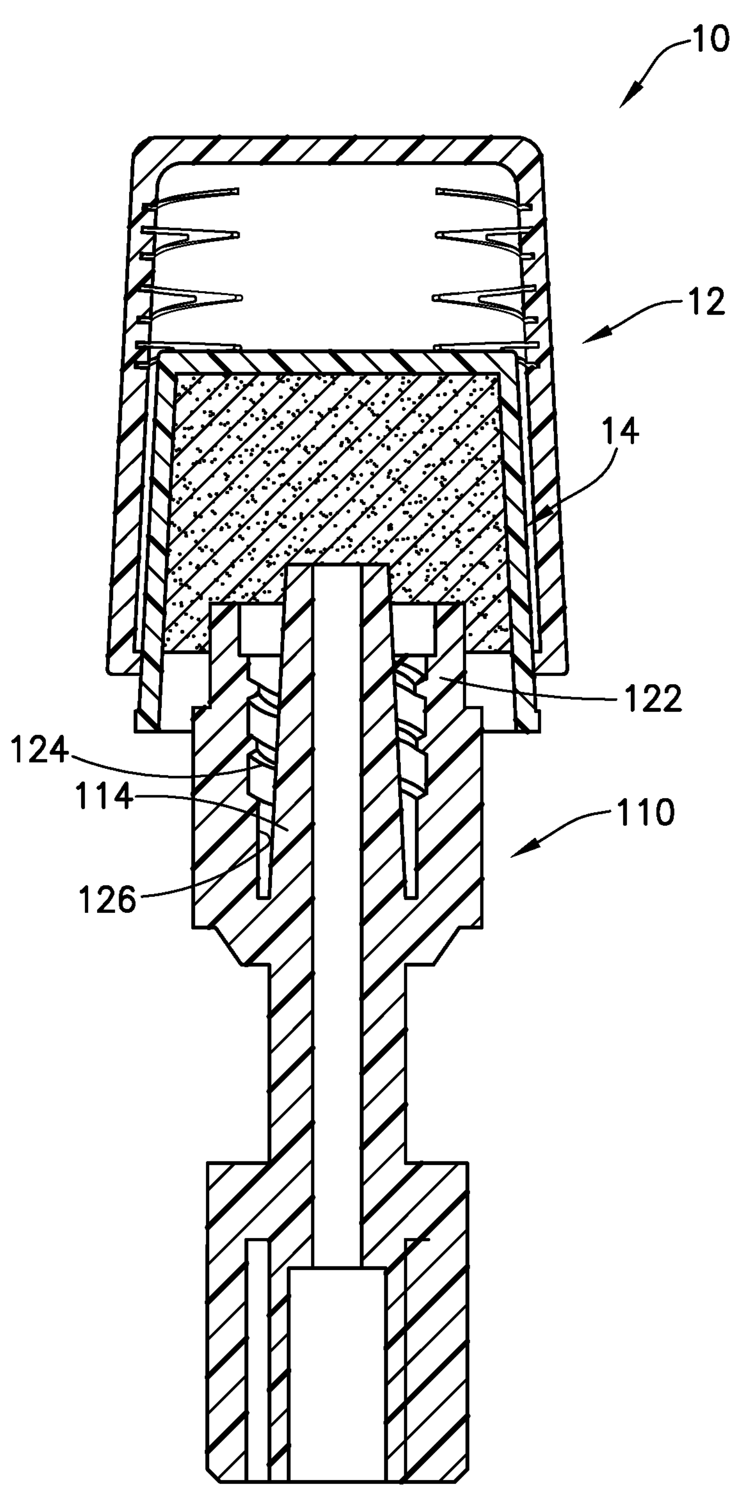
FIG. 5D is a cross-sectional view showing the male needleless connector of FIG. 5C inserted into the cap of FIG. 2A, according to an aspect of the present disclosure.

As previously described, the cap 10 of the present disclosure is a disinfecting cap 10 configured to be connected to various types and sizes of needleless connectors 110, 112. For example, FIGS. 5A and 5B show the cap 10 being connected to a female luer connector 112. FIGS. 5C and 5D show the cap 10 being connected to a male luer connector 110.

In order to connect the cap 10 to a male or female needleless connector 110, 112, the practitioner first removes any packaging from the cap 10 and removes the protective cover 54 (if present) from the bottom end 30 of the inner housing 14. The practitioner can also remove the clamp 56 (if present) so that the inner housing 14 can move freely into the outer housing 12.

Once the packaging, protective cover 52, and clamp 56 are removed, the cap 10 is ready for use to be connected to the connector 110, 112. The cap 10 is shown in this ready for use position in FIG. 3A. In particular, as shown in FIG. 3A, the cap 10 is in the initial or extended position with the bottom end 30 of the inner housing 14 extending outside of the outer housing 12. In order to attach the connector 110, 112 to the cap 10, the practitioner first moves the cap 10 toward the connector 110, 112 inserting the bottom end 30 of the inner housing 14 over the connector 110, 112. In particular, for the female connector 112, the bottom end 30 is inserted over the opening 116 and septum 118 of the female connector 112. Continuing to move the female connector 112 into the housing 12 brings outer surfaces 130 and corresponding threads 128 of the female connector 112 into contact with the circular top 48 and/or cylindrical outer surface 52 of the absorbent member 16. In a similar manner, for the male connector 110, the bottom end 30 is inserted over the stem 114. Continuing to move the male connector 110 into the housing 112 brings outer surfaces of the stem 114 into contact with portions of the absorbent member 16.

Once the connector 110, 112 is inserted into the inner housing 14, the practitioner applies an axially directed pressure to the outer housing 12 and/or to the connector 110, 112 (as shown by arrows A1 and A5 in FIG. 3A) causing the inner housing 14 to retract into the outer housing 12 and causing the threaded pin 62 or inner guide 36 of the inner housing 12 to move through the vertical slot 44 of the outer guide 28 or track towards the segments 40, 42 of the outer guide 28. Continuing to move the inner housing 14 into the outer housing 12 moves the pin 62 or inner guide 36 into the clockwise and counterclockwise segments 40, 42 of the outer guide 28 or track, as shown in FIG. 3B. As previously described, these segments 40, 42 cause the inner housing 14 to alternate between rotating in the clockwise direction (shown by arrow A2 in FIG. 3B) and the counterclockwise direction (shown by arrow A3 in FIG. 3B) relative to the outer housing 12 and the connector 110, 112. Rotating the inner housing 14 over the connector 110, 112 causes the absorbent member 16 to press against and scrub surfaces of the connector 110, 112 to mechanically remove particles from the surfaces of the connector 110, 112. Also, the contact with the connector 110, 112 causes the absorbent member 16 to compress, which releases the cleaning or disinfecting solution from the absorbent member 16. The released cleaning solution cleans and disinfects surfaces of the connector 110, 112. Also, the cleaning or disinfecting solution can contact particles, such as biological materials (e.g., microorganisms, cells, or bacteria), that are scrubbed from the connector 110, 112 to destroy such biological materials.

Continuing to press against the top end 18 of the outer housing 12 and/or continuing to press the connector 110, 112 into the outer housing 12 causes the inner housing 14 to continue to rotate back-and-forth scrubbing the surfaces of the connector 110, 112 as the inner housing 14 retracts farther into the outer housing 12. Eventually, the inner guide 36 or protrusion travels to a proximal or top end of the outer guide 28 or track, meaning that the inner housing 14 stops rotating and is fully seated or retracted within the outer housing 12. The inner housing 14 is shown in this final or fully retracted position in FIG. 3C. As previously described, in this fully retracted position, the locking tabs 46 automatically move to the deployed position (as shown in FIGS. 2B and 6A-6C) to prevent the inner housing 14 from being removed from the outer housing 12. At this point, the cap 10 is fully engaged to the connector 110, 112 and can remain in place on the connector 110, 112 for an extended period of time, such as for up to seven days, which is a maximum use time allowed by many medical facility protocols.

In order to remove the cap 10 from the connector 110, 112, the practitioner grasps the cap 10 and/or connector 110, 112 and pulls the cap 10 away from the connector 110, 112. Pulling the cap 10 away from the connector 110, 112 causes the inner guide 36 to move through the segments 40, 42 of the outer guide 28, as previously described, meaning that the inner housing 14 rotates relative to the outer housing 12 and the connector 110, 112. The inner housing 14 continues to move through the outer housing 12 eventually contacting the deployed locking tabs 46, which block further axial movement of the inner housing 14 relative to the outer housing 12 and prevent the inner housing 14 from being removed from the outer housing 12. With the inner housing 14 in contact with the locking tabs 46, the practitioner pulls the cap 10 away from the connector 110, 112, which releases the cap 10 from the connector 110, 112. Once the connector 110, 112 is fully released or removed from the cap 10, the connector 110, 112 can be connected to a VAD. For example, the connector 110, 112 can be attached or inserted into a hub, port, or valve of the VAD forming a needleless fluid-tight connection between the connector 110, 112 and a fluid path, channel, or lumen of the VAD.

Manufacturing Method for a Disinfecting Cap with Multi-Part Housing

The caps 10 of the present disclosure are intended to be single-use disposable medical devices that can be used for covering a medical connector (e.g., the male luer connector 110 or the female luer connector 112) during a single medical procedure or event. The cap 10 can be discarded after the single use. As such, the cap 10 desirably is inexpensive and easy to manufacture by known commercial manufacturing processes, such as injection molding.

Figure 8A:
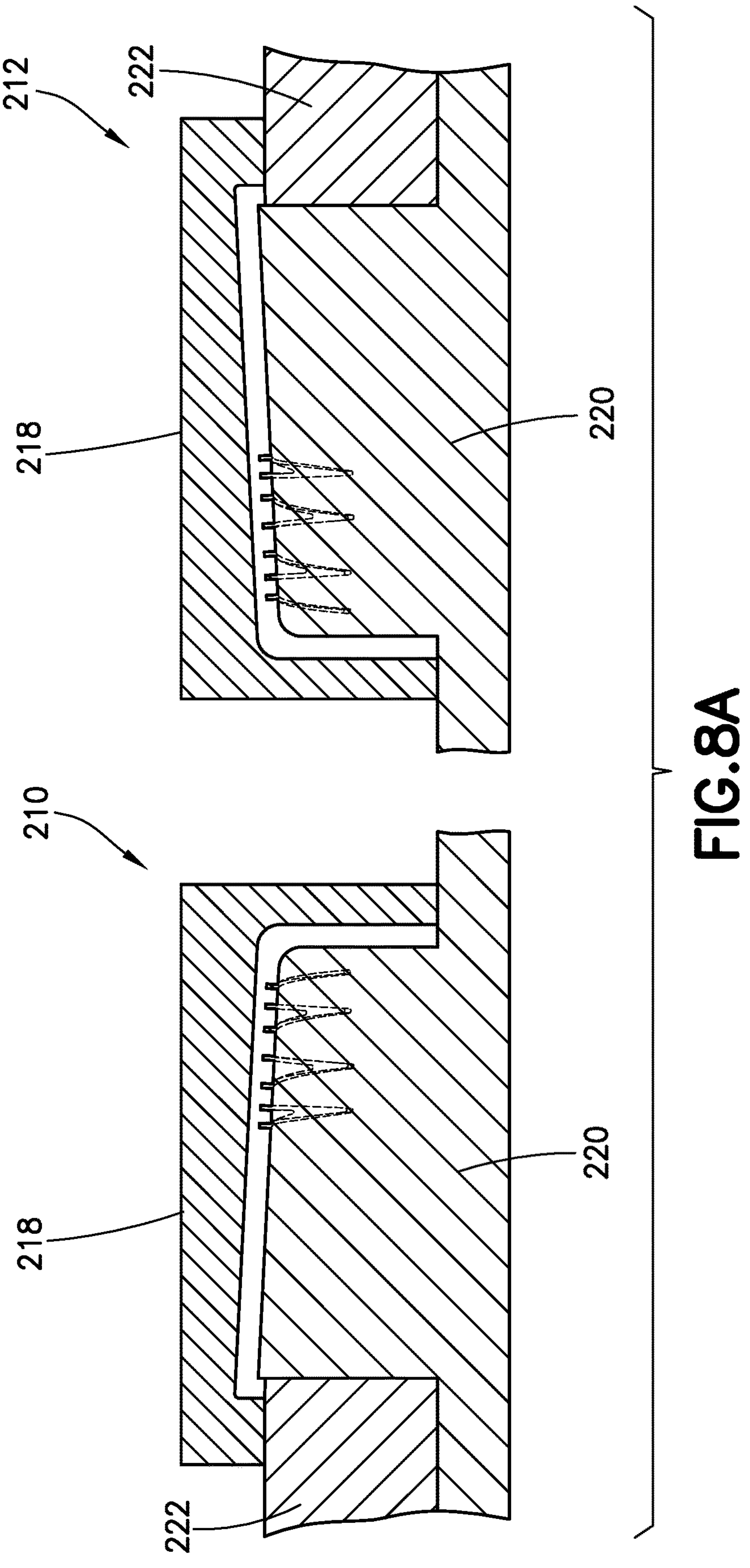
FIG. 8A is a schematic drawing showing molds for making parts of an outer housing of a disinfecting cap, according to an aspect of the present disclosure.
Figure 8B:
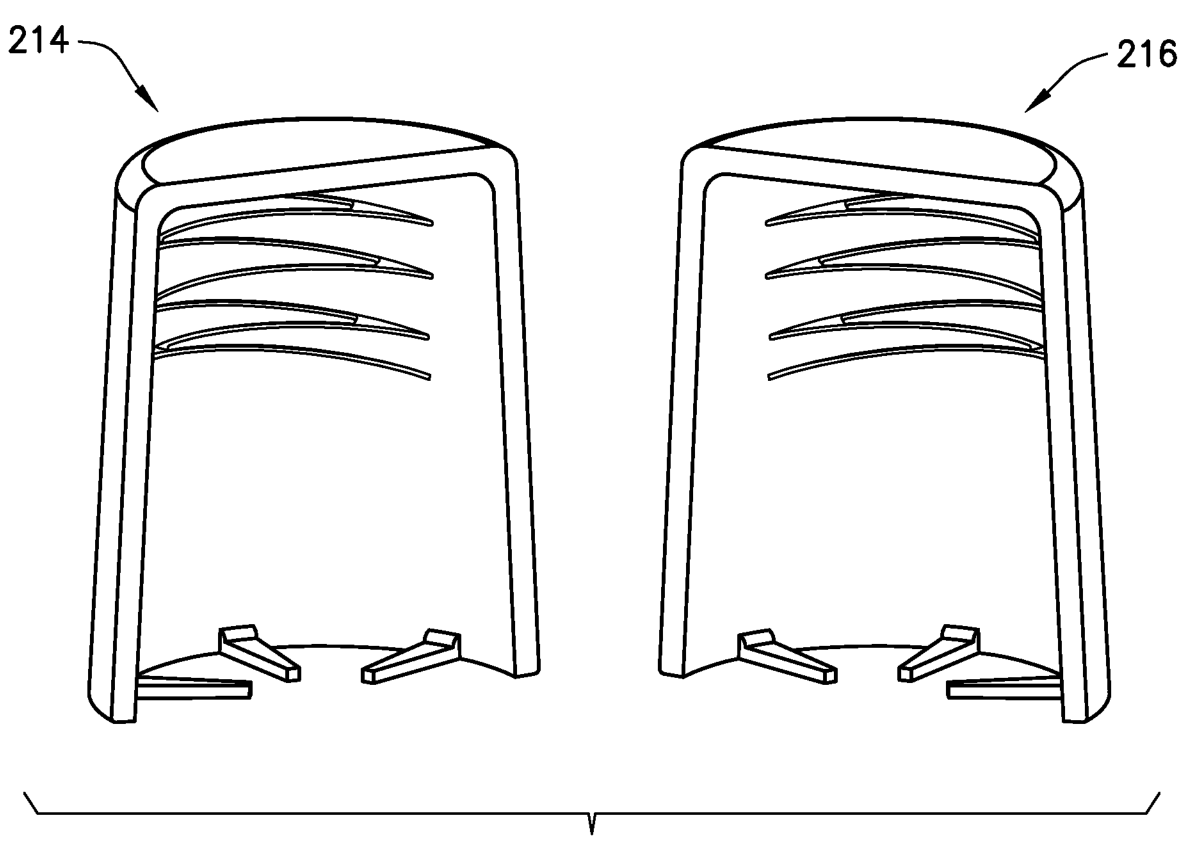
FIG. 8B shows perspective views of parts of the outer housing made using the molds of FIG. 8A.
Figure 8C:
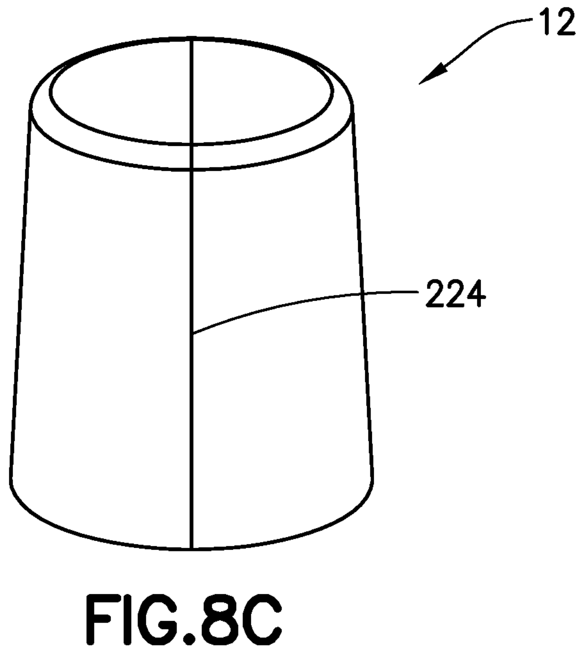
FIG. 8C is a perspective view of an outer housing of a disinfecting cap made by ultrasonic welding of the parts of FIG. 8B, according to an aspect of the present disclosure.

FIGS. 8A-8C show aspects of a molding and assembly process for making the caps 10 of the present disclosure. In particular, FIG. 8A shows molds 210, 212 that can be used for forming parts 214, 216 of the outer housing 12. The molds 210, 212 can be a three-piece mold comprising a cavity 218, a core 220 comprising protrusions for forming the segments 40, 42 of the outer guide 28, and a side core 222 for forming the bottom end 20 of the outer housing 12. FIG. 8B shows the parts 214, 216 of the outer housing 12 prior to assembly. FIG. 8C shows the outer housing 12 made by assembling the parts 214, 216.

The method of making the cap 10 includes a first step of making the outer housing 12. Specifically, the outer housing 12 can be made by forming the first part 214 and the second part 216 in the molds 210, 212. For example, the parts 214, 216 can be made by a common plastic molding process, such as injection molding. After the parts 214, 216 are formed and removed from the molds 210, 212, the parts are assembled to form the outer housing 12. For example, the parts 214, 216 can be joined together by ultrasonic welding at a welded joint 224 (shown in FIG. 8C).

The method also includes a step of making the inner housing 14. Unlike the outer housing 12, the inner housing 14 can be a single molded part formed by, for example, a single injection molding step. The method also includes making the absorbent member 16. For example, the absorbent member 16 can be made by cutting or stamping a foam part of a desired shape and size from a larger foam part or sheet. In other examples, the absorbent member 16 can be formed by molding or extrusion processes, as are known in in the art.

After the outer housing 12, inner housing 14, and absorbent members 16 are made, the method includes a final step of assembling the cap 10. For example, assembly can include inserting the absorbent member 16 into the inner housing 14. As previously described, the absorbent member 16 can be retained within the inner housing 14 by a friction fit and/or using various fasteners or adhesives. The method also includes partially inserting the inner housing 14 into the outer housing 12. In order to insert the inner housing 14 into the outer housing, the inner guide 36 is aligned with the vertical slot 44 of the outer housing 12. The inner housing 14 is then advanced axially into the outer housing 12 to the initial or extended position (shown in FIGS. 2A and 3A). Once the inner housing 14 is in the desired position, the removable clamp 56 (shown in FIGS. 7A and 7B) can be attached to the inner housing 14 to retain the inner housing 14 in the initial or extended position and to prevent the inner housing 14 from being prematurely inserted farther into the outer housing 12.

While examples of the disinfecting cap 10 and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A disinfecting cap for a needleless connector, the cap comprising:

an outer housing comprising a first end, an open second end, a sidewall extending between the first end and the second end, and at least one outer guide on an inner surface of the sidewall;

an inner housing comprising a first end, an open second end sized to receive a distal end of the needleless connector, a sidewall extending between the first end and the second end, and at least one inner guide on an outer surface of the sidewall that interacts with the at least one outer guide of the outer housing; and at least one absorbent member disposed in the inner housing configured to contain a cleaning solution for cleaning and/or disinfecting portions of the needleless connector engaged to the cap, wherein movement of the at least one inner guide relative to the at least one outer guide causes the inner housing to move axially into the outer housing and to alternate between rotating in a first direction and rotating in a second direction relative to the outer housing.

2. The cap of claim 1, wherein the inner housing is configured to move between an extended position, where the second end of the inner housing is outside of the outer housing, and a retracted position, where the inner housing is entirely in the outer housing.

3. The cap of claim 2, wherein movement of the at least one inner guide relative to the at least one outer guide, as the inner housing moves from the extended position to the retracted position, causes the inner housing to rotate back-and-forth multiple times as the inner housing advances to the retracted position.

4. The cap of claim 3, wherein the inner housing rotates back-and-forth at least four times as the inner housing moves from the extended position to the retracted position.

5. The cap of claim 1, wherein the needleless connector comprises a male luer connector or a female luer connector.

6. The cap of claim 1, wherein the at least one outer guide comprises a track extending inwardly from the inner surface of the sidewall of the outer housing, and wherein the track comprises alternating segments for rotation in the first direction connected in series with segments for rotation in the second direction.

7. The cap of claim 6, wherein the track comprises a groove or slot extending into the sidewall of the outer housing.

8. The cap of claim 6, wherein the at least one inner guide comprises a protrusion extending radially outward from the outer surface of the sidewall of the inner housing received within the track of the outer housing.

9. The cap of claim 6, wherein the track further comprises a longitudinally extending groove or slot extending between the open second end of the outer housing and a distal end of one of the of segments of the track positioned to receive the at least one inner guide as the inner housing is inserted into the outer housing.

10. The cap of claim 6, wherein the segments of the track are non-helical extending about the inner surface of the outer housing by less than a full rotation.

11. The cap of claim 6, wherein each alternating segment causes the inner housing to rotate by an angular distance of from about 45 degrees to about 270 degrees about a longitudinal axis of the inner housing.

12. The cap of claim 1, wherein the rotation of the inner housing about the needleless connector inserted into the inner housing causes the at least one absorbent member to scrub the needleless connector inserted in the inner housing.

13. The cap of claim 1, wherein the outer housing further comprises at least one tab that is pressed to a recessed position when the inner housing is in an extended position and which moves to a blocking position preventing removal of the inner housing from the outer housing, when the inner housing is inserted into the outer housing moving towards the retracted position.

14. The cap of claim 13, wherein the at least one tab is pivotally connected to the inner surface of the sidewall of the outer housing and biased to pivot away from the inner surface of the sidewall to the blocking position.

15. The cap of claim 13, wherein the at least one tab moves automatically from the recessed position to the blocking position upon insertion of the inner housing into the outer housing.

16. The cap of claim 1, wherein the outer housing comprises a plurality of tabs that are biased to a recessed position when the inner housing is in an extended position and which move to a blocking position preventing removal of the inner housing from the outer housing, when the inner housing is inserted into the outer housing moving towards the retracted position, and wherein the plurality of tabs comprise a plurality of elongated members having a first end connected to the sidewall of the outer housing and a second end configured to protrude into a space defined by the sidewall of the outer housing for blocking removal of the inner housing from the outer housing.

17. The cap of claim 1, further comprising the cleaning solution absorbed by the at least one absorbent member, the cleaning solution comprises Isopropyl Alcohol (IPA) and/or chlorhexidine gluconate.

18. The cap of claim 1, further comprising a removable clamp configured to be connected to the inner housing when the inner housing is in an extended position, which prevents insertion of the inner housing into the outer housing until the clamp is removed from the inner housing.

19. A manufacturing method for the cap of claim 1, the method comprising:

forming a first part of the outer housing in a first mold;

forming a second part of the outer housing in a second mold;

attaching the first part to the second part by ultrasonic welding to form the outer housing;

forming the inner housing by a single molding process;

inserting the at least one absorbent member into the inner housing; and inserting the inner housing into the formed outer housing.

20. A method of using the cap of claim 1, comprising:

inserting a distal end of the needleless connector into the open second end of the inner housing, such that a surface of the at least one absorbent member contacts the distal end of the needleless connector; and pressing the outer housing toward the needleless connector causing the inner housing to rotate relative to the outer housing and to the needleless connector for scrubbing surfaces of the needleless connector.

* * * * *